(12) United States Patent
Clifton

(10) Patent No.: US 11,568,540 B2
(45) Date of Patent: Jan. 31, 2023

(54) SYSTEM, METHOD, AND COMPUTER-READABLE MEDIUM FOR REJECTING FULL AND PARTIAL BLINKS FOR RETINAL TRACKING

(71) Applicant: OPTOS PLC, Scotland (GB)

(72) Inventor: David Clifton, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 609 days.

(21) Appl. No.: 16/594,934

(22) Filed: Oct. 7, 2019

(65) Prior Publication Data

US 2021/0104041 A1  Apr. 8, 2021

(51) Int. Cl.
*G06T 7/00* (2017.01)
*G06T 7/33* (2017.01)
*G06T 7/246* (2017.01)
*A61B 3/10* (2006.01)
*A61B 3/14* (2006.01)

(52) U.S. Cl.
CPC ............ *G06T 7/0014* (2013.01); *A61B 3/102* (2013.01); *A61B 3/14* (2013.01); *G06T 7/248* (2017.01); *G06T 7/337* (2017.01); *G06T 2207/10016* (2013.01); *G06T 2207/20182* (2013.01); *G06T 2207/30041* (2013.01)

(58) Field of Classification Search
USPC ......... 382/103, 128, 218, 117, 224; 351/206
See application file for complete search history.

(56) References Cited

U.S. PATENT DOCUMENTS 5,455,601 A * 10/1995 Ozaki .................... G09G 5/399
                                                              345/158

(Continued)

FOREIGN PATENT DOCUMENTS

CN       109543629 A    3/2019
JP       2004-504684 A  2/2004
(Continued)

OTHER PUBLICATIONS

Sarvaiya et al., Image Registration by Template Matching Using Normalized Cross-Correlation, 2009 IEEE 978-0-7695-3915, DOI 10.1109/ACT.2009.207, pp. 819-822. (Year: 2009).*
D. Padfield "Masked Object Registration in the Fourier Domain", IEEE Transactions on Image Processing, vol. 21, No. 21, on May 5, 2012.
J. P. Lewis, entitled "Fast Normalized Cross-Correlation," In: Vision Interface, 1995, pp. 120-123.

(Continued)

*Primary Examiner* — Ishrat I Sherali
(74) *Attorney, Agent, or Firm* — Delucia, Mlynar & Associates LLP

(57) ABSTRACT

A method, system, and computer-readable medium, for detecting whether an eye blink or non-blink is captured in the image. The method includes filtering, from the image, one or more objects that are predicted to be unsuitable for determining whether an eye blink or no-blink is captured in the image, to provide a filtered image. The method also includes correlating the filtered image with a reference image, and determining, based on the correlating, whether the eye blink or non-blink is captured in the image. The eye blink is a full eye blink or a partial eye blink, and the images may be sequentially captured IR SLO images, in one example embodiment herein. Images determined to include an eye blink can be omitted from inclusion in a final (e.g., OCT) image.

22 Claims, 14 Drawing Sheets

(56) References Cited

U.S. PATENT DOCUMENTS

| | | | |
|---|---|---|---|
| 5,815,242 | A | 9/1998 | Anderson et al. |
| 9,687,143 | B2 * | 6/2017 | Satake ............... A61B 3/18 |
| 9,924,862 | B2 | 3/2018 | Brown et al. |
| 10,849,499 | B2 * | 12/2020 | Ono ............... A61B 3/0025 |
| 2010/0110275 | A1 | 5/2010 | Mathieu |
| 2011/0280446 | A1 * | 11/2011 | Steinberg ........... H04N 5/23219 |
| | | | 382/103 |
| 2015/0272432 | A1 | 10/2015 | Satake et al. |
| 2016/0104036 | A1 * | 4/2016 | Tsou ............... G06V 40/19 |
| | | | 382/171 |
| 2016/0302658 | A1 * | 10/2016 | Cherchi ............... A61B 3/0041 |
| 2017/0188822 | A1 * | 7/2017 | Yang ............... G06T 7/73 |
| 2019/0059720 | A1 | 2/2019 | Kubota |
| 2019/0059723 | A1 | 2/2019 | Ono |

FOREIGN PATENT DOCUMENTS

| | | |
|---|---|---|
| JP | 2017-153543 A | 9/2017 |
| JP | 2018-206252 A | 12/2018 |
| JP | 2019-041841 A | 3/2019 |

OTHER PUBLICATIONS

S. Mondal et al., entitled "Image Similarity Measurement using Region Props, Color and Texture: An Approach", International Journal of Computer Applications (0975-8887), vol. 121, No. 22, Jul. 2015, pp. 23-26.

"Second moment of area", Wikipedia, accessed Oct. 3, 2019. Available at: https://en.wikipedia.org/wiki/Second_moment_of_area.

Zhang et al., "Retinal Vessel Segmentation Using Gabor Filter and Textons", Proc 18th Conf. on Medical Image Understanding and Analysis (MIUA), 2014, pp. 1-6.

Extended European Search Report (EESR) dated Mar. 11, 2021, in European Application No. EP 202000486.

Notice of Reasons for Refusal dated Jan. 26, 2022 in Japanese patent application No. 2020-170119; English-language machine translation attached (6 sheets).

Awais, Muhammad et al. "Automated Eye Blink Detection and Tracking Using Template Matching", 2013 IEEE Student Conference on Research and Development, MY, IEEE, Dec. 16-17, 2013, p. 79-83.

* cited by examiner

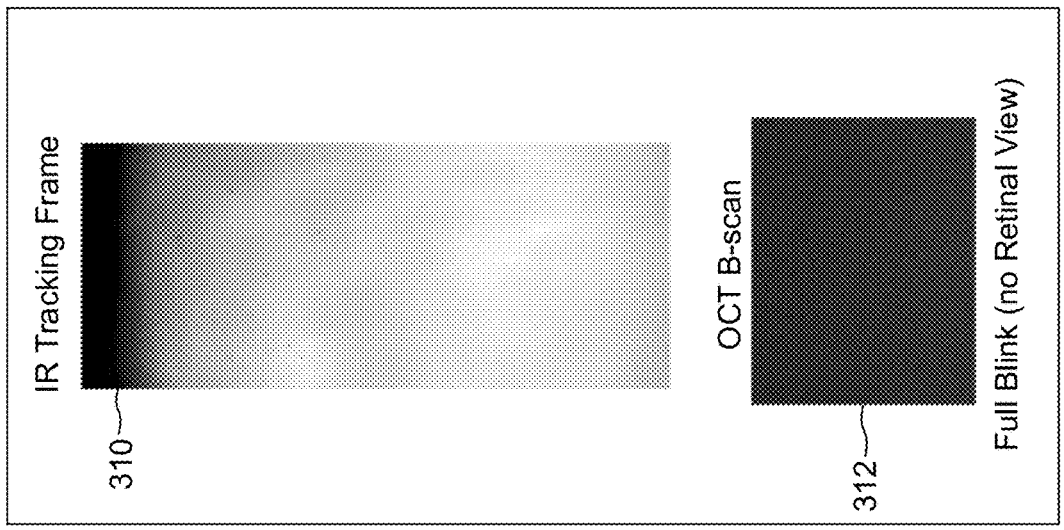
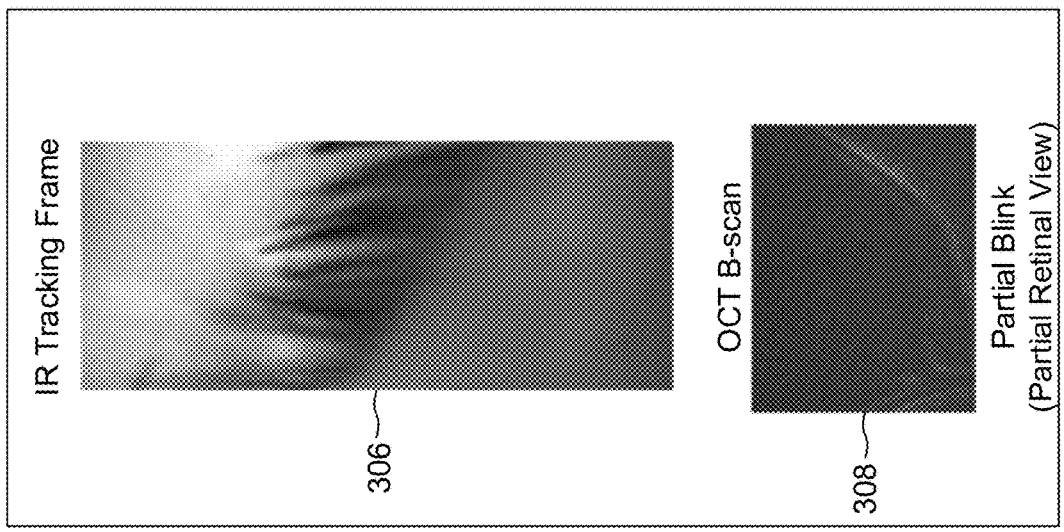
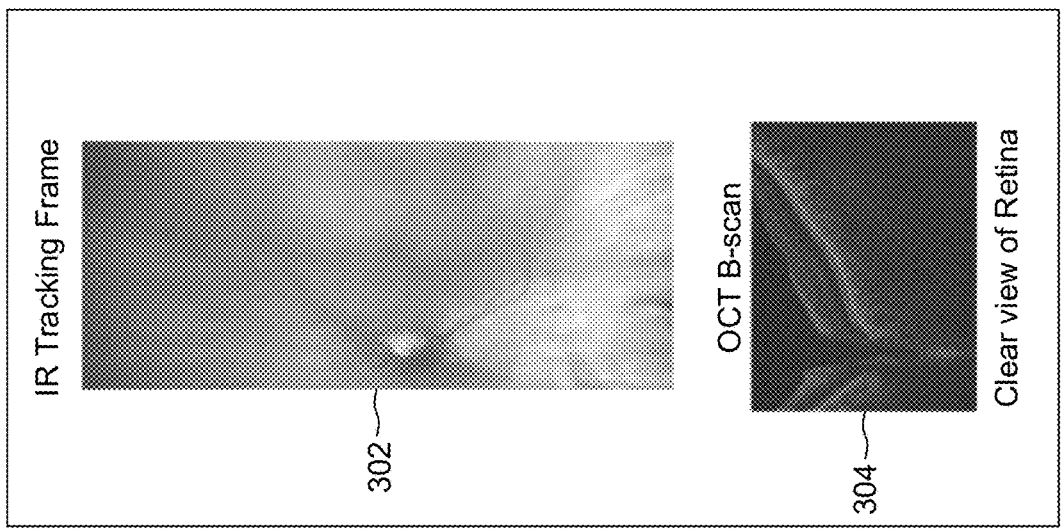
Fig. 3c
Fig. 3b
Fig. 3a

SYSTEM, METHOD, AND COMPUTER-READABLE MEDIUM FOR REJECTING FULL AND PARTIAL BLINKS FOR RETINAL TRACKING

FIELD

Example aspects herein relate generally to retinal tracking, and, in particular, to a system, method, and computer-readable medium for detecting and rejecting full and partial blinks in retinal tracking.

BACKGROUND

Optical coherence tomography (OCT) is a well-known interferometric imaging technique which is widely used in ophthalmology as a power diagnostic tool, for imaging the retinal structure of a subject. OCT is an interferometric technique whereby an illumination source is directed towards the retina of the subject and the reflected beam, or sample arm, is combined with light in a controlled reference arm, and whereby the interference properties of the combined beam are used to determine and display the structure of the imaged retina. OCT imaging techniques can capture two-dimensional and three-dimensional images from within a subject's eye by using low-coherence light. OCT typically employs near-infrared light, based on low-coherence tomography, wherein relatively long wavelength light can penetrate into the eye.

It also is well known to image the retina of a subject using a Scanning Laser Ophthalmoscope (SLO) to obtain an image of the retina at multiple wavelengths, where specific wavelengths represent specific layers of the retina. SLO generally involves confocal laser scanning microscopy, and utilizes horizontal and vertical scanning mirrors to scan, by example, a particular retinal region, and create raster images that can be displayed. Although OCT and SLO scanners may be distinct devices, in at least some cases they can be provided together in a combined SLO-OCT scanner, and their scans can be synchronized in time. In such combined SLO-OCT scanners, at least some of the same scanner elements are used in both SLO and OCT techniques, but different lasers are fired in parallel.

When capturing images of a subject's retina using the above techniques, full blinking (i.e., closing of an eyelid), partial blinking, and/or no blinking of the subject's eye, can occur. Full or partial blinking can be detrimental to the outcome of the imaging techniques, because such blinking can at least partially obstruct the scanner's view of the retina. An OCT scan taken during conditions of full or partial blinking can result in an OCT frame stack (e.g., having both averages B-scans and C-scans) that includes "unclear" images resulting from the full or partial blink conditions. Such a frame stack, when viewed as an assembled image, may include unwanted artefacts, and may suffer from an overall reduction in quality relative to a case where only clear images (i.e., those taken during non-blinking conditions, where the scanner has a clear view of the retina) are included in the frame stack. Also, eye blinks can cause a retina tracking system to lose its correct position and thus corrupt a scan position and hence final scan images (e.g., OCT images). Thus, it would be useful to be able to accurately distinguish between clear and unclear images, and to be able to selectively omit unclear images so that they are not included in a final frame stack.

FIGS. 3a to 3c represent examples of clear images and unclear images. More particularly, FIG. 3a shows an example of a tracking frame (e.g., an infrared (IR) tracking frame) 302 obtained by an IR SLO as a result of the SLO scanning a patient's retina during a condition where there was no blinking (and thus the SLO had a clear view of the retina), and a corresponding OCT B-scan 304 obtained in synchronization with the tracking frame 302, by OCT scanning, during the same condition. For convenience, such a condition will hereinafter be referred to as a "clear view condition" or "non-blink condition", and the frame 302 and OCT B-scan 304 also are referred to as "clear images".

FIG. 3b shows an example of a tracking frame 306 obtained by the IR SLO as a result of the SLO scanning the patient's retina during a condition where there was partial blinking (and thus the SLO had only a partial view of the retina), and a corresponding OCT B-scan 308 obtained in synchronization with the tracking frame 306, by OCT scanning, during the same condition. For convenience, such a condition will hereinafter be referred to as a "partial blink condition" or "partial retinal view condition"), and the frame 306 and OCT B-scan 308 also are referred to as "unclear images".

FIG. 3c shows an example of a tracking frame 310 obtained by the IR SLO as a result of the SLO scanning the patient's retina during a condition where there was a full blink (and thus the scanner had no view of the retina), and a corresponding OCT B-scan 312 obtained in synchronization with the tracking frame 310, by OCT scanning, during the same condition. For convenience, such a condition will hereinafter be referred to as a "full blink condition" or "no retinal view condition"), and the frame 310 and OCT B-scan 312 also are referred to as "unclear images".

Analysis of the OCT frames 304, 308, 312 directly could provide some indication of whether the content of the frames indicates the occurrence of full or partial blinks. However, in practice, those types of analyses have proven to be ineffective owing to the images typically having low information content and poor signal-to-noise characteristics. Also, in a simple version of blink detection, it might be envisaged that variations in mean image intensity of returned light could be used to determine that a blink is occurring. However, experimentation has shown that this is not typically the case, because there is a wide range of common intensity characteristics found during blink and non-blink conditions. This is especially true during peripheral scans, where a range of returned intensities can commonly be in the same range for blink (unclear) and retinal (clear) images. In other words, there may be a general similarity between a blink characteristic image and a peripheral retinal image. Indeed, peripheral scans may result in images that are similar to those shown in FIG. 3c for the full blink condition scenario. Thus, it can be ineffective or inadequate to attempt to employ such simple, intensity based, parameterization techniques to attempt to distinguish between obscured (blink and partial blink) and non-obscured (non-blink) scans.

SUMMARY

The foregoing and other limitations are overcome by a method, system, and computer-readable medium, according to example aspects herein, for detecting whether an eye blink or non-blink is captured in an image. According to an example embodiment herein, the method comprises filtering, from the image, one or more objects that are predicted to be unsuitable for determining whether an eye blink or non-blink is captured in the image, to provide a filtered image. The method also includes correlating the filtered image with a reference image, and determining, based on the correlating, whether the eye blink or non-blink is captured in the image. Images determined to include an eye blink can be omitted from inclusion in a final (e.g., OCT) image.

The eye blink may be a full eye blink or a partial eye blink. The image preferably is captured after the reference image, in sequence, and both images preferably are IR SLO images, in one example embodiment herein. In one example embodiment herein, both of the images are obtained as part of a "live" stream of images as a result of IR scanning of a patient's eye, wherein the reference image (e.g., image frame n−1) was captured immediately prior to the image (e.g., image frame n) in sequence, and wherein the reference image (which is used for blink/non-blink detection) also is filtered as described above, before the correlating is performed.

Also according to an example embodiment herein, the determining comprises determining a score based on a result of the correlating, wherein the score indicates a presence or absence of a characteristic, and the characteristic is, in one example, a peak characteristic.

In one example embodiment herein, the absence of the characteristic indicates that the eye blink (e.g., a full or partial blink) is captured in the image, and the presence of the characteristic indicates that a retina is captured in the image, but no eye blink.

In still a further example embodiment herein, the method further comprises performing spatial directional filtering to the image prior to the filtering.

Additionally, in an example embodiment herein, the filtering comprises detecting the one or more objects, in the image, determining that the one or more objects belong to one or more predetermined classifications, and removing the one or more objects from the image, to provide the filtered image.

The method further can comprise segmenting each of the image and the reference image into segments, prior to the filtering, at least for a case in which the method is performed to detect whether a partial blink is captured in the image.

BRIEF DESCRIPTION OF THE DRAWINGS

Embodiments of the invention will now be explained in detail, by way of non-limiting example only, with reference to the accompanying drawings, the contents of which are described below. Like reference numerals appearing in different figures of the figures denote identical, corresponding or functionally similar elements, unless indicated otherwise.

FIG. 3a shows example consequences on scan quality when IR SLO and OCT B-scans are performed during a non-blinking condition (i.e., a clear view of retina).

FIG. 3b shows example consequences on scan quality when IR SLO and OCT B-scans are performed during a partial blink condition (i.e., a partial retinal view).

FIG. 3c shows example consequences on scan quality when IR SLO and OCT B-scans are performed during a full blink condition (i.e., no retinal view).

DETAILED DESCRIPTION OF EMBODIMENTS

Figure 1:
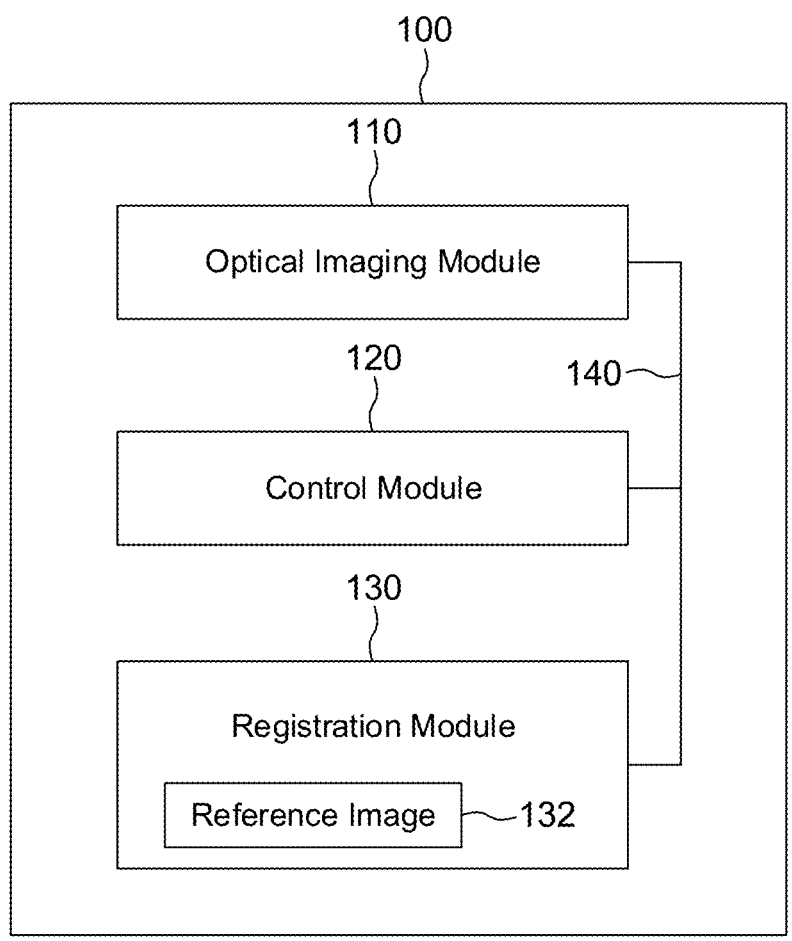
FIG. 1 is a schematic illustration of an optical system according to an example embodiment herein.

Example embodiments herein will now be described in detail with reference to the accompanying drawings.

As described above, conventional analyses for detecting whether image frame content is indicative of blinking or non-blinking conditions according to known optical imaging techniques, have proven to be ineffective for the above-described reasons. The inventor has discovered that it would be of far greater efficacy to identify unclear (and clear) images based on "tracking" images (e.g., IR SLO images) used to track retinal motion, because those types of images (which may be captured in parallel, and time-synchronized, with OCT frames) typically contain more direct information indicative of blinks, and generally have much higher informational quality than OCT frames. IR SLO tracking frames used to track retinal motion typically are captured by illuminating the retina at non-visible IR wavelengths. This is because the illumination is continuous through a scan set-up period, as well as during the scan. If visible wavelengths were to be employed for illumination, on the other hand, then brightness as well as a duration of the illumination would be uncomfortable to the patient (and also would produce closing of the iris, which, in turn, would limit the amount of light leading to a compromise in image quality).

Human blinks typically occur with durations greater than several frame sample intervals. As such, the inventor also has discovered that blink (or non-blink) conditions can be detected based on a comparison of at least two (or more) frames (e.g., IR SLO frames) obtained at a frame rate of, by example, at least 50 samples per second to capture a fastest blink rate (e.g., typically about 1/10 th of a second). This translates to about 5 frames in the case of a 1/10 th second blink.

As such, methods and systems are described herein for detecting blink and non-blink conditions in images, according to an example aspects herein. In accordance with a method of an example aspect herein, sequentially obtained images (e.g., which may be obtained as a stream of images as a result of IR scanning of a patient's eye) are filtered by a spatial directional filter. Then, object filtering is performed to the filtered images, wherein, in one example embodiment herein, object filtering is performed by one or more object filters "tuned" to filter (e.g., remove) detected objects in the filtered images based on predetermined characteristics (constraints) associated with blink and/or non-blink conditions (or retinal characteristics). After the object filtering, cross-correlation is performed for at least two sequential ones of the images filtered by the object filter, to determine whether a result of the cross-correlation indicates a blink or non-blink condition, as indicated by, for example, an absence or presence, respectively, of a cross-correlation peak. Images determined to indicate a blink condition can be omitted from a final image (e.g., an OCT image), since they likely not suitable for image (or sub-region) selection and tracking, whereas images determined to indicate a non-blink condition can be included in the final image, since they are likely to include trackable retinal features.

In some example embodiments herein, in a case in which the foregoing method is employed for detecting whether images indicate a partial blink condition, images from the image stream first can be segmented into vertical blocks or segments, before the filterings and cross-correlation are performed for the segments. In this case, one or more correlation peaks can be obtained as a result of cross-correlating corresponding sets of the segments, in order to determine whether sufficient retinal features (or an absence of such features) are present during a partial blink. This can be helpful given that a scan region of an OCT typically is less than the region of the IR SLO. In fact, it can be a horizontal line in some scan modes.

Processing of SLO images in the ways described above may improve reliability of SLO image registration and eye tracking, allowing the imaging region of the OCT scanner of the SLO/OCT imaging system to be more accurately maintained at a desired target location and thus enabling an improved OCT image to be produced.

A schematic illustration of an example medical imaging device 100 that can be employed to perform scanning of a subject's retina, and which can be operated according to example methods described herein, will now be described, with reference to FIG. 1.

The medical imaging device 100 of the present example embodiment comprises an optical imaging module 110, a control module 120, and a registration module 130. The optical imaging module 110, the control module 120, and the registration module 130 are communicatively coupled by any appropriate communication channel 140 (such as a data bus or the like) so as to be capable of exchanging data with one another, as described in more detail below.

The optical imaging module 110 can be any kind of optical imaging apparatus that is operable to generate image data defining an image of a region of any part of the human or animal body (the region being either on an external surface of the body part, or an internal section of the body part), by firstly acquiring samples whose values are indicative of an optical property of the body part at the respective sample locations in the region. By way of an example, the optical imaging module 110 may comprise an image sensor (such as a charge-coupled device (CCD) or complementary MOS (CMOS) sensor, for example) or more generally any kind of photodetector capable of generating image data by measuring an intensity of light transmitted through the body part, or reflected from the imaged region of the body part, or light derived from the transmitted/reflected light, such as light resulting from an interference of the transmitted/reflected light with a reference light signal, for example, at a plurality of sample locations. The sample values acquired by the optical imaging device 110 may be indicative of at least one optical property of the body part, such as its reflectance, transmittance, fluorescence or other form of photoluminescence, and/or color, for example.

The image data generated by the optical imaging module 110 can be any numerical representation of the image derived from the acquired samples, such as bitmap image defined by an array of pixels whose locations in the array and values are indicative of the acquired sample values and sample locations, respectively. The optical imaging module 110 may employ a mapping to map the acquired samples to corresponding pixels of the image such that an indication of the sample location of each sample is mapped to a pixel location of a corresponding pixel of the image. The sample value of each sample may be assigned or otherwise mapped to a pixel value of a corresponding pixel of the image. In one example embodiment herein, the generated bitmap image may be stored, without compression, in a raw format (e.g. as the raw bitmap, without a header or other information such as size information) in a memory device of the optical imaging module 110, for increased processing speed. The generated bitmap image may, however, alternatively be stored in the memory device in any known compressed image file format, for example in a standardized compressed bitmap file such as GIF, PNG, TIFF or JPEG.

The medical imaging device 100 may be provided in one of many different forms. By way of an example, the medical imaging device 100 of the present example embodiment is provided in the form of a retinal scanner for imaging a region of the retina of a patient's eye. It should be understood, however, that the configurational and operational aspects of the retinal scanner described in the following are not particular to retinal scanners and are applicable to other kinds of medical scanner and medical imaging device.

The retinal scanner may, as in the present example embodiment, be a scanning laser ophthalmoscope (SLO) for imaging the surface of the retina. The retinal scanner may, for example, take the form of a wide-field SLO having an optical arrangement as described, for example, in U.S. Pat. No. 5,815,242, the contents of which are incorporated herein by reference in their entirety, or alternatively a narrower-field SLO of a conventional type well-known to those versed in the art. The retinal scanner may alternatively be one of a number of known optical coherence tomography (OCT) scanners that are configured to acquire OCT image data defining an image of a region of the retina at a prescribed depth beneath its surface. As a further alternative, the retinal scanner may be a combined SLO-OCT scanner, which is capable of acquiring both a confocal fundus image via the SLO optics and a tomographic image via the OCT optics in a single procedure. An example of a wide-field combined SLO-OCT scanner is described in U.S. Pat. No. 9,924,862, the contents of which are incorporated herein by reference in their entirety.

The retinal scanner may image the region by scanning a collimated beam of light along the region and measuring, for each sample location of a sequence of sample locations on the region covered by the scan, the intensity of light reflected from the respective sample location using an image sensor or other photodetector arrangement that is capable of measuring the intensity of the reflected light, thus obtaining a sequence of samples of the intensity of the reflected light. For each acquired sample, the retinal scanner forms an association (for example, by storage in an appropriately configured data structure, which may be visualized as a table or the like) between the sample value and the values of one or more scan parameters (for example, one or more control signals for controlling the angular displacement of one or more scanning elements of the retinal scanner) that are indicative of the corresponding sample location.

The control module 120 may control the optical imaging module 110 to acquire a sequence of samples in accordance with a scan pattern (e.g., a dense scan pattern), the scan pattern being such, in the generation of the image data by the optical imaging module 110, sample locations on the retina of the acquired samples are mapped to corresponding pixel locations in the image that are arranged in an array. The scan pattern may be a raster scan pattern, in which case the sequence of acquired samples is mapped onto a corresponding sequence of pixels whose ordering reflects the ordering of the acquired samples in accordance with the raster scan pattern. The control module 120 thus controls the optical imaging module 110 to perform a scan using a scan pattern of one of the different kinds described above, for example, thereby devoting the available scan time to the acquisition of image data defining an image of a relative small portion of the retina, with the spacing of adjacent sample points on the retina typically being similar to the optical resolution of the optical imaging module 110.

In an optical imaging module comprising one or more scanning elements as described above, the control module 120 may generate control signals for driving the rotation of the scanning element(s) on the basis of the function, so that the collimated light is scanned across the retina in accordance with the sparse scan pattern defined by the function. During the scan, the optical imaging module 110 may acquire samples at a constant sampling rate (e.g., the frame rate discussed above), as in the present example embodiment, or, for other scenarios, at irregular intervals.

The registration module 130 is configured to register the image defined by the generated image data against a reference image 132 stored therein, which, in one example embodiment, includes image data defining an image of at least a part of the region that has been imaged by the optical imaging module 110. In one example embodiment herein, the area of the retina imaged in the reference image 132 may be larger than the area of the retina covered by a single scan of the kind described above that is performed by the optical imaging module 110.

The registration module 130 may register the image against the reference image 132 by calculating a cross-correlation between the image and the reference image 132. For example, the registration module 130 may, as in a present example embodiment, be configured to register the image against the reference image 132 by calculating a Weighted Normalized Cross-correlation (in other words, a Masked Normalized Cross-correlation) between the image and the reference image 132. Further details of how the Weighted Normalized Cross-correlation calculation may be performed are provided in, for example, the article titled "Masked Object Registration in the Fourier Domain" by D. Padfield, published in IEEE Transactions on Image Processing, Vol. 21, No. 21, on 5 May 2012 ("the Padfield publication"), the contents of which are incorporated herein by reference in their entirety. This technique allows registration of sparse image data by considering only genuine data points; non-data points in a sparse image frame are excluded from the registration computation by use of a mask. The registration module 130 of the present example embodiment is thus configured to produce a measure of a translation offset between two images. The registration module 130 may be configured to register the image directly against the reference image 132, or indirectly by registering image against a previously acquired image (which, in that case, forms the reference image 132) in a sequence of images acquired by the optical imaging module 110, wherein a difference of the aforementioned kind(s) between the previously acquired image and the reference image 132 is known.

In the present example embodiment, the reference image 132 used by the registration module 130 is acquired prior to the performance of the registration by the registration module 130, for example by forming a mosaic of images of adjacent imaging areas on the retina that are each imaged by the optical imaging module 110 using a scan pattern. The adjacent imaging areas preferably overlap in order to allow the images to be registered against each other so that they can be combined (or stitched together) to generate the mosaic of images forming the reference image 132.

The medical imaging device 100 may, as in the present example embodiment, be configured such that each incoming image frame (acquired with using the sparse scan pattern as described above) is registered against the reference image 132 to determine a translation offset and, if the offset is greater than a specific threshold, the scan pattern is re-centered to follow any movement. This may allow for a greater degree of translation offset whilst still remaining within range of the scan pattern.

In another example embodiment herein, the reference image 132 is one of the incoming image frames obtained as part of a "live" stream of images as a result of scanning of a patient's eye, wherein the reference image (e.g., image frame n−1) 132 was captured immediately prior to a present one of the incoming image frames (e.g., image frame n) in sequence.

Figure 2:
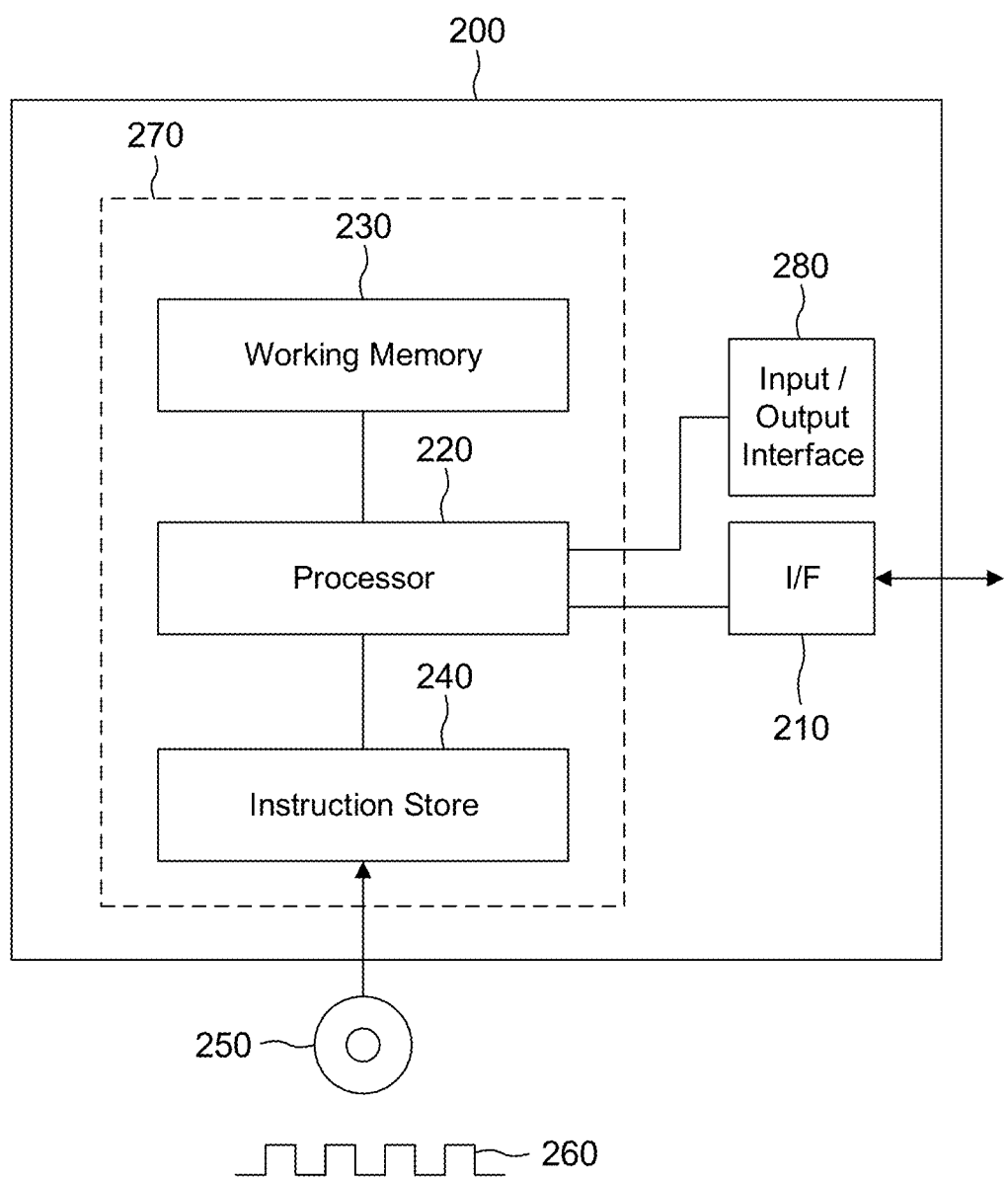
FIG. 2 is a schematic illustration of a programmable signal processing hardware according to an example embodiment herein.

FIG. 2 is a schematic illustration of a programmable signal processing hardware 200, which may be configured to control a medical imaging device comprising an optical imaging module 110 as described above, and, in particular, function as the control module 120 and/or the registration module 130. The programmable signal processing hardware 200 comprises a communication interface (I/F) 210 for receiving sample data acquired by the optical imaging module 110, and sending control instructions to the optical imaging module 110 to control the optical imaging module 110 to acquire samples in accordance with a scan pattern and, optionally, based on offsets obtained in the registration (in order to maintain the scan location on a region of interest on the retina, so as to compensate for movements of the eye during imaging). The signal processing apparatus 200 further comprises a processor (e.g. a Central Processing Unit, CPU, or Graphics Processing Unit, GPU) 220, a working memory 230 (e.g. a random access memory) and an instruction store 240 storing a computer program comprising the computer-readable instructions which, when executed by the processor 220, cause the processor 220 to perform various functions including those of the control module 120, and/or the registration module 130, and the methods described herein. The working memory 230 stores information used by the processor 220 during execution of the computer program, including image data generated by the optical imaging device 110, the reference image 132, one or more offsets calculated during the image registration, one or more functions defining the scan pattern, and the candidate imaging templates described below, for example. The instruction store 240 may comprise a ROM (e.g. in the form of an electrically-erasable programmable read-only memory (EEPROM) or flash memory) which is pre-loaded with the computer-readable instructions. Alternatively, the instruction store 240 may comprise a RAM or similar type of memory, and the computer-readable instructions of the computer program can be input thereto from a computer program product, such as a non-transitory, computer-readable storage medium 250 in the form of a CD-ROM, DVD-ROM, etc. or a computer-readable signal 260 carrying the computer-readable instructions. In any case, the computer program, when executed by the processor, causes the processor to execute a method of controlling a medical imaging device 100 as described herein. It should be noted, however, that the control module 120 and/or the registration module 130 may alternatively be implemented in non-programmable hardware, such as an application-specific integrated circuit (ASIC). An input/output user interface 280 also can be included in the hardware 200, connected to the processor 200. The user interface 280 can include any suitable type of interface for enabling a user to input information to the processor 200, and/or any suitable type output interface for enabling a user to perceive information output from the processor 200.

In the present example embodiment, a combination 270 of the hardware components shown in FIG. 2, comprising the processor 220, the working memory 230 and the instruction store 240, is configured to perform functions of the control module 120 and/or the registration module 130.

Figure 4A:
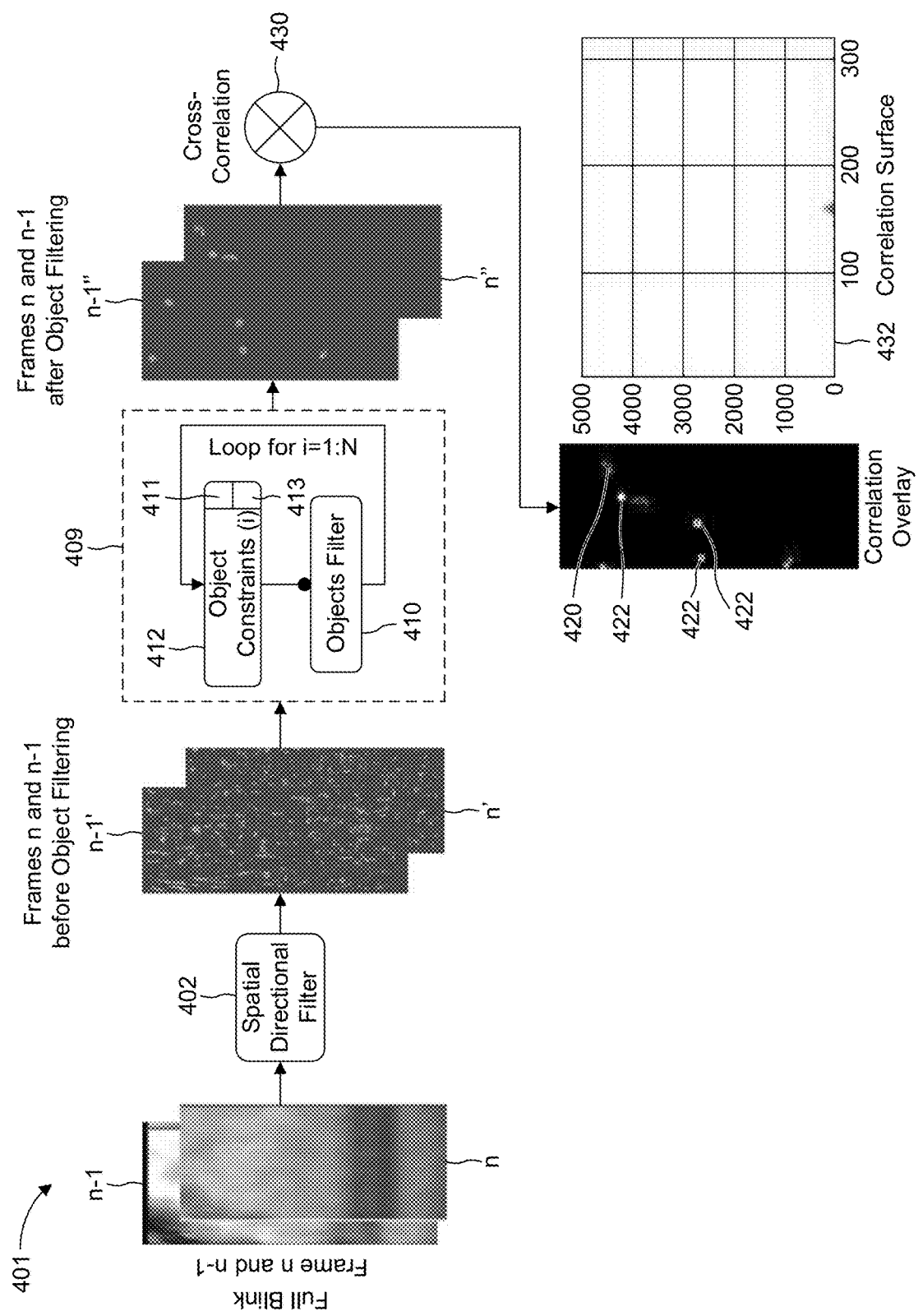
FIG. 4a shows an example representation of a system for detecting a full blink condition in at least one image, according to an example aspect herein.
Figure 4B:
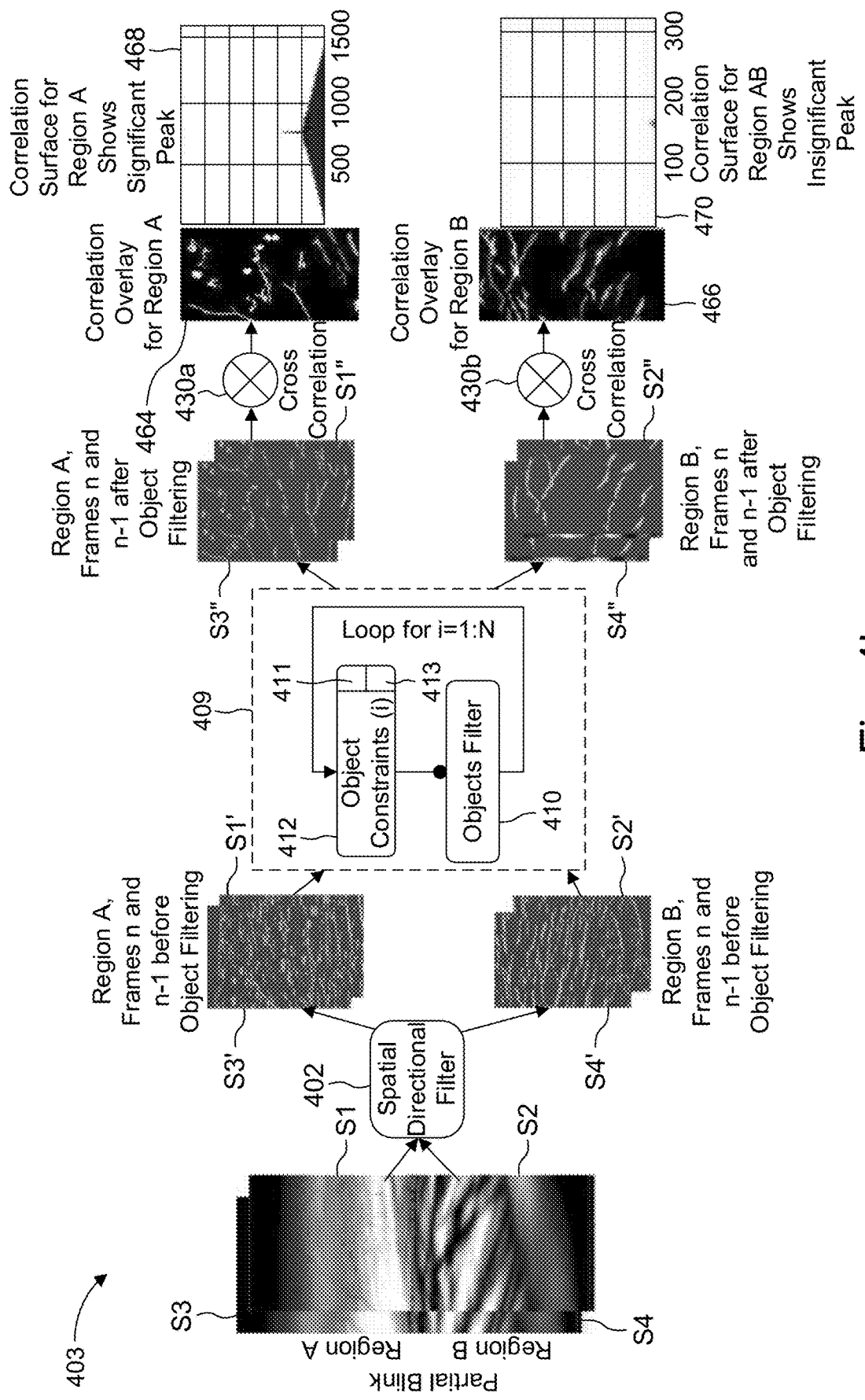
FIG. 4b shows an example representation of a system for detecting a partial blink condition in at least one image, according to an example aspect herein.
Figure 4C:
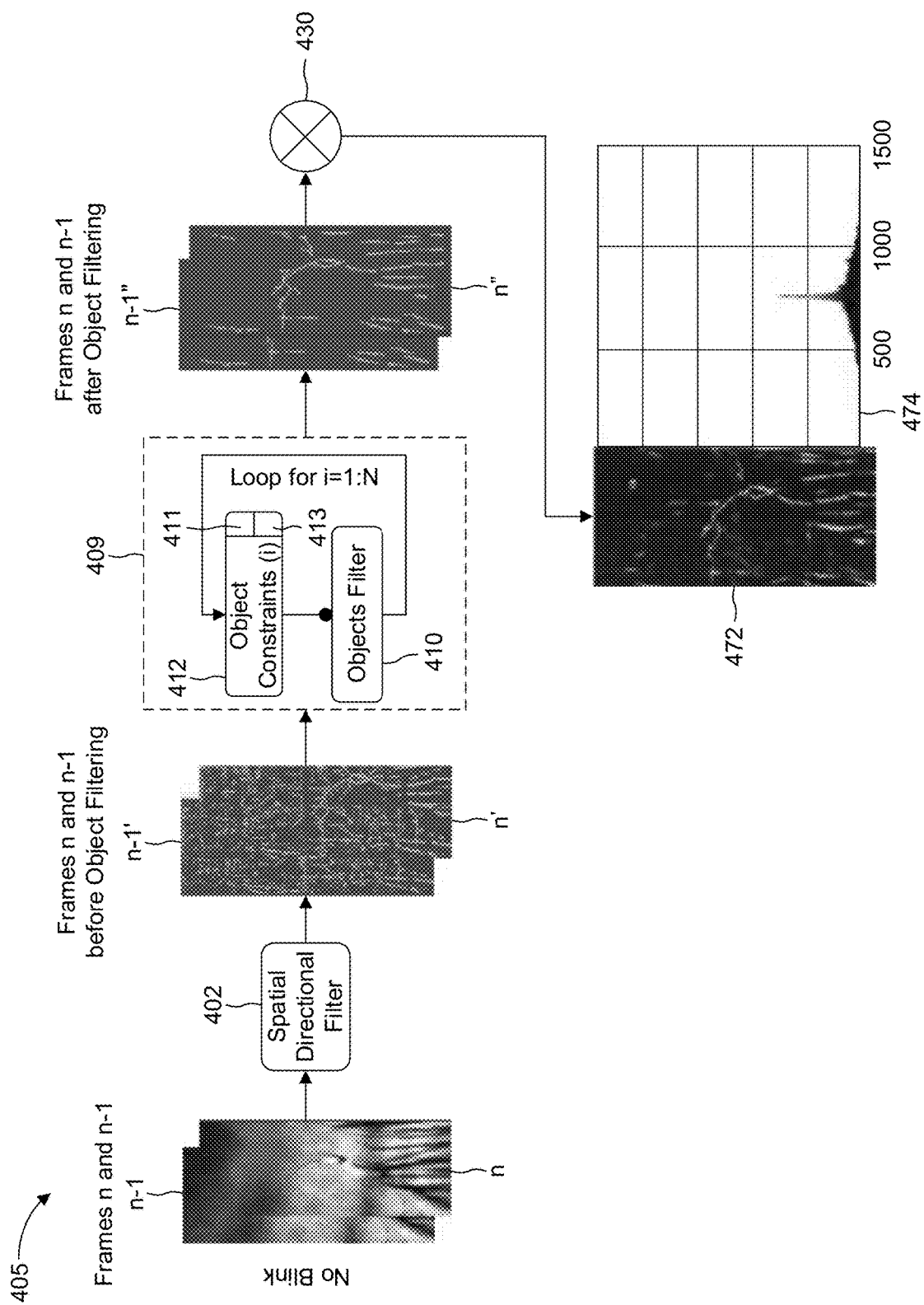
FIG. 4c shows an example representation of a system for detecting a non-blink condition in at least one image, according to an example aspect herein.
Figure 5A:
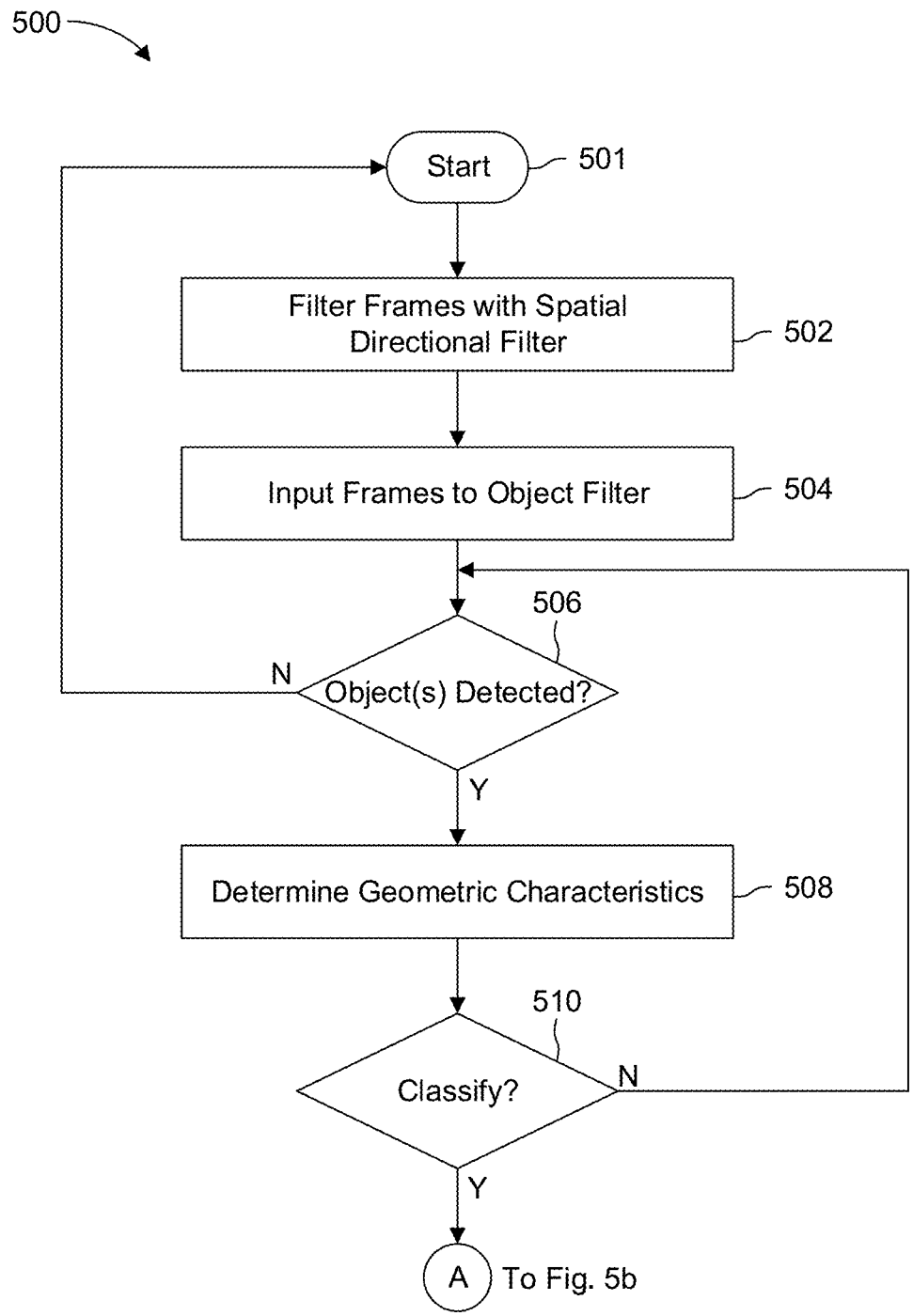
FIG. 5A illustrates a flow diagram of a method for detecting a full blink condition in at least one image, according to an example aspect herein.
Figure 5B:
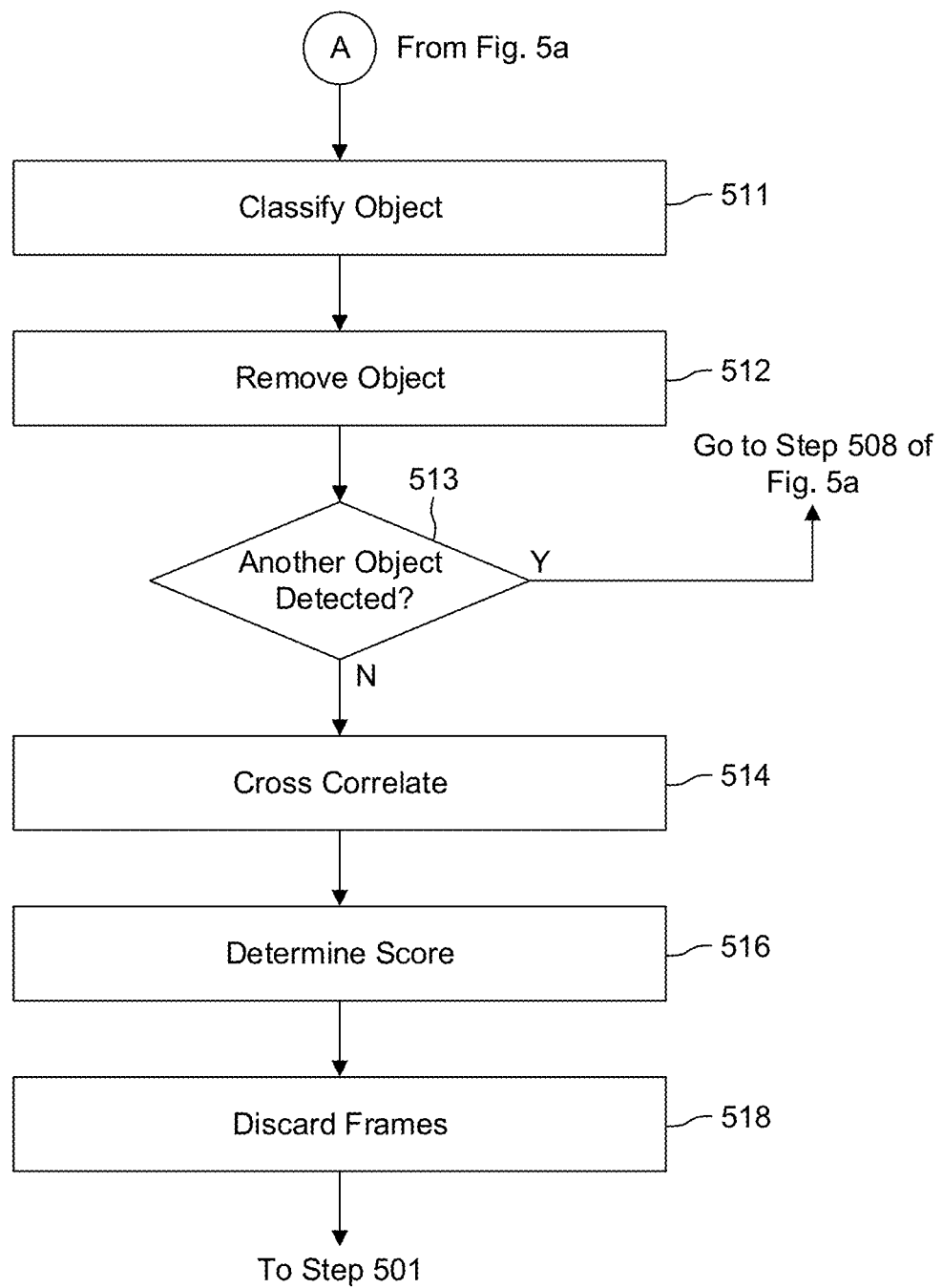
FIG. 5B illustrates a flow diagram of a method for detecting a full blink condition in at least one image, according to an example aspect herein.
Figure 6A:
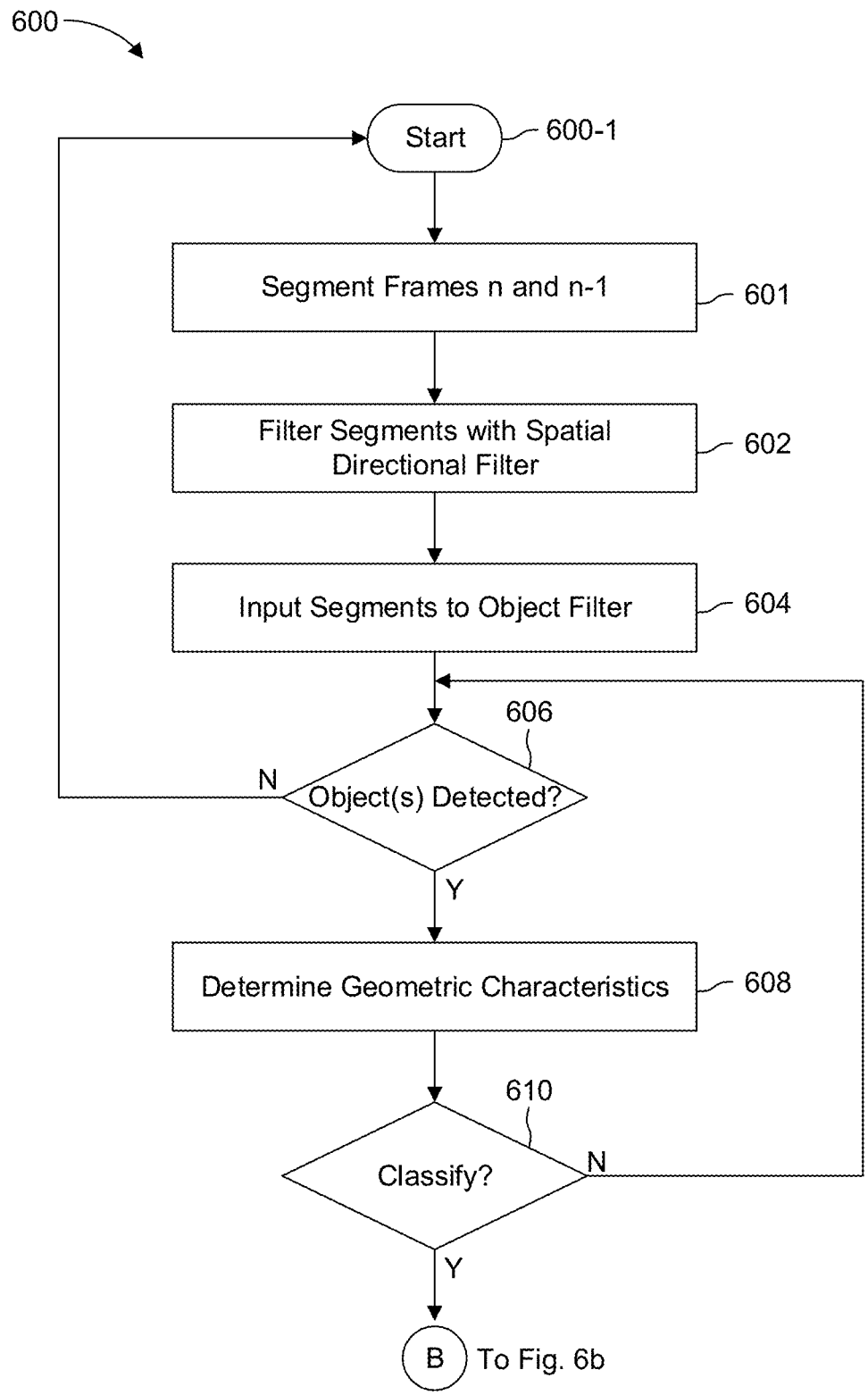
FIG. 6A illustrates a flow diagram of a method for detecting a partial blink condition in at least one image, according to an example aspect herein.
Figure 6B:
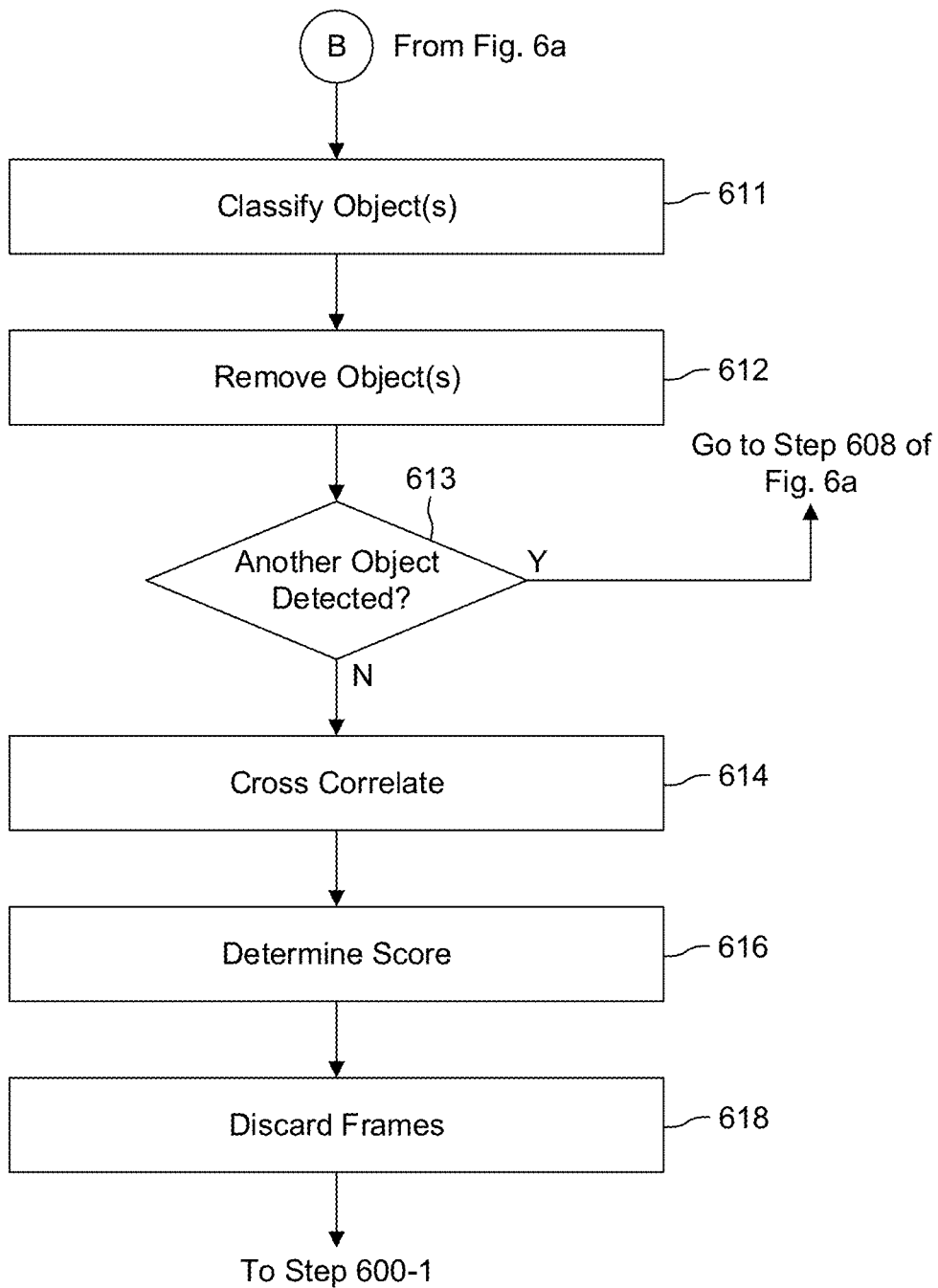
FIG. 6B illustrates a flow diagram of a method for detecting a partial blink condition in at least one image, according to an example aspect herein.
Figure 7A:
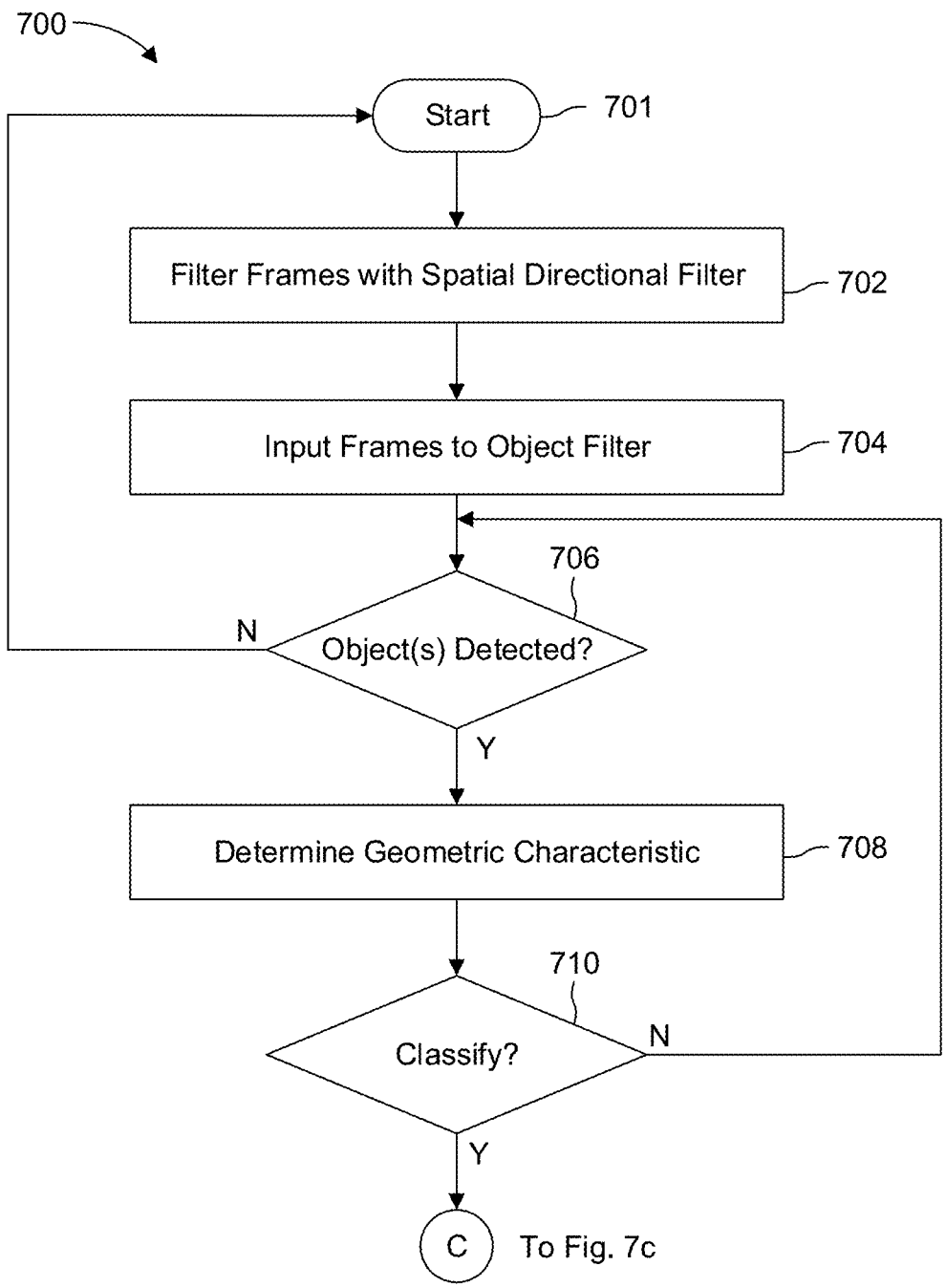
FIG. 7A illustrates a flow diagram of a method for detecting a non-blink condition in at least one image, according to an example aspect herein.
Figure 7B:
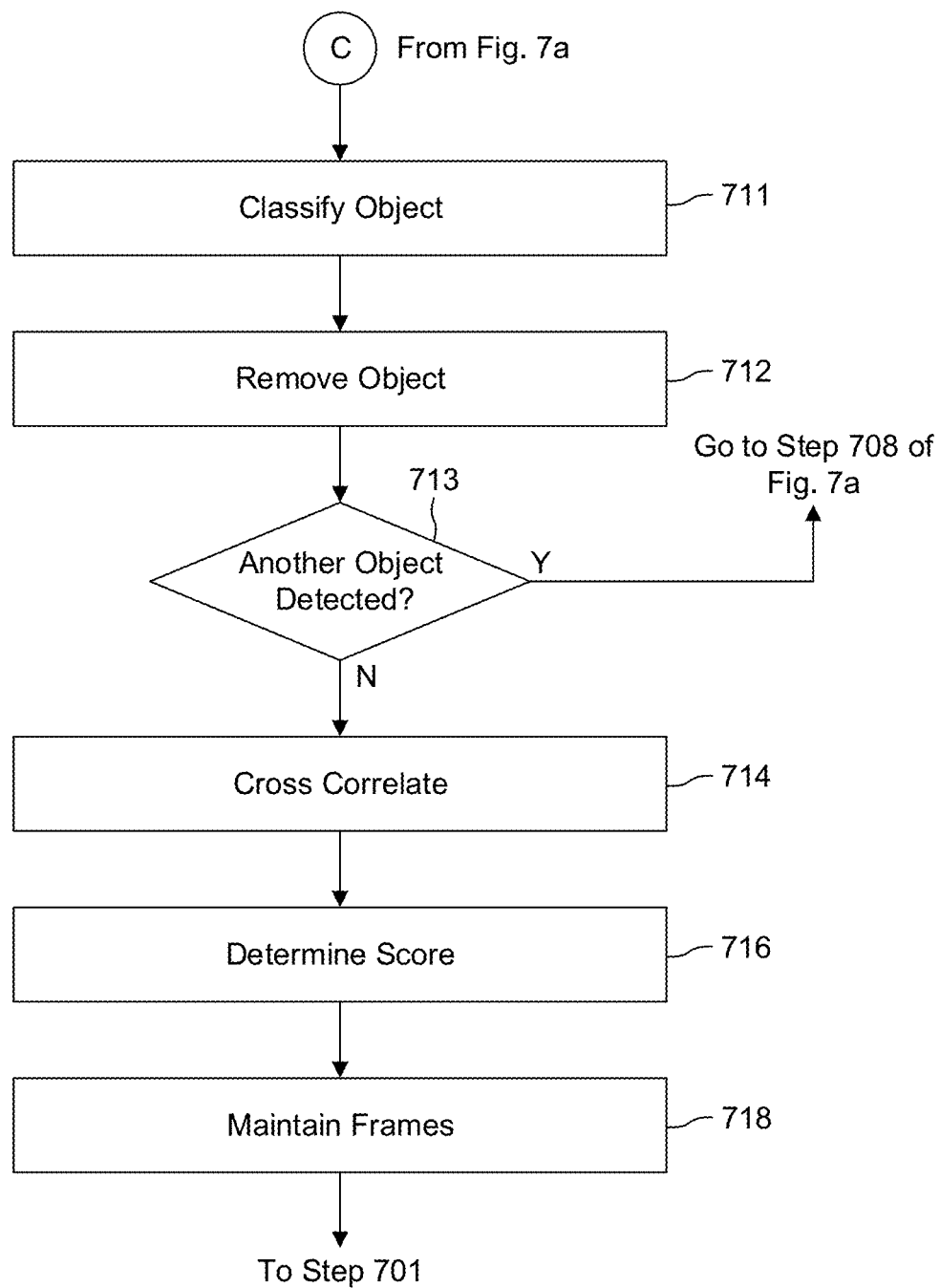
FIG. 7B illustrates a flow diagram of a method for detecting a non-blink condition in at least one image, according to an example aspect herein.

Having described FIGS. 1 and 2, methods and systems according to example aspects herein will now be described, with reference to FIGS. 4a to 4c and 5 to 7. FIG. 4a shows a system 401 and FIGS. 5a and 5b show a method 500, for detecting a full blink condition in at least one image, FIGS. 4b shows a system 403 and FIGS. 6a and 6b show a method 600, for detecting a partial blink condition in at least one image, and FIG. 4c show a system 405 and FIGS. 7a and 7b show a method 700, for detecting a non-blink condition in at least one image. Each system 401, 403, and 405 can be operated, and each method 500, 600, and 700 can be performed, separately, in parallel, simultaneously, or at different times, and/or each can be operated to process the same images from a same image stream simultaneously or separately, or each may process different input image frames. In some example embodiments herein, components 402, 409, 430, 430a, and 430b of FIGS. 4a-4c may be included in processor 220 and/or instruction store 240 of FIG. 2 described above, components 430, 430a, 430b may be included in registration module 130 of FIG. 1 described above, and the image stream may be obtained as described above from system 100 via interface 210, for being used as inputs to the systems 401, 403, 405 and methods 500, 600, 700. Also, components 432, 468, 470, and 474 of FIGS. 4a-4c may be included in (or be formed by) user interface 280 of FIG. 2. In some examples herein, image frames n and n−1 in the image stream are IR SLO images (e.g., captured by system 100), and those images are used as a reference for capturing OCT images (e.g., by system 100).

Procedure 500 and system 401 will first be described. In step 501 (FIG. 5a) the method 500 commences with an image frame n and a previously obtained image frame n−1 (e.g., from an image stream obtained via interface 210 as described above) being input to the system 401, wherein in one example embodiment herein, frame n−1 was captured immediately prior to frame n in sequence. Then in step 502 the frames n and n−1 are applied to a spatial directional filter 402, wherein the frames n and n−1 are filtered. In one example embodiment herein, the spatial directional filter 402 operates as an x- and y-directional filter used to compute derivatives in those respective directions, although the spatial directional filter 420 instead may do so with respect to any selected direction within a given space. In one example embodiment herein, the spatial directional filter 402 is an edge detector that can determine first derivatives of an image. The first derivatives (or slopes) typically are evident where a large change occurs between adjacent pixel values. That is, edges within the image frames n and n−1 may be visible owing to a large change (a steep gradient) between adjacent pixel values, as determined by the spatial directional filter 402. The determined derivatives can be scaled to show only negative, zero, and positive slopes, as determined by the application of interest. Also, in one example embodiment herein, the spatial directional filter 402 is a Gabor filter, and operates as described in the publication by Zhang et al., entitled "Retinal Vessel Segmentation Using Gabor Filter and Textons", Proc. $18^{th}$ Conf. on Medical Image Understanding and Analysis (MIUA), 2014, pp. 1-6, which is incorporated by reference herein in its entirety. A Gabor filter may involve "directional" rotations (e.g., by 8 angles in 360/8 steps), in one example embodiment.

According to an example embodiment herein, the spatial directional filter 402 performs filtering by removing predetermined features from the frames n and n−1, such as, by example and without limitation, background lighting, high frequency noise, and/or other predetermined undesired features (i.e., features deemed not useful for tracking retinal information). Also, in one example embodiment herein, the spatial directional filter 402 can include a series of spatial-directional filters (not shown), wherein each such filter operates by filtering a respective type of feature from the frames n and n−1.

As a result of the image frames n and n−1 being filtered by the spatial directional filter 402 in step 502, the spatial directional filter 402 outputs corresponding filtered frames n' and n−1', wherein frame n' is a version of frame n filtered by the filter 402 as described above, and frame n−1' is a version of frame n−1 filtered by the filter 402 as described above.

In step 504, the filtered frames n' and n−1' are input to a filter 409, which comprises an object filter 410 and object constraints 412. In one example embodiment herein, the object constraints 412 are employed by the object filter 410 in a manner as will be described below, to determine whether to classify objects that may be included in the frames n' and n−1', as being within one or more predetermined classifications 411 (if at all). The object constraints 412 include predetermined classifications 411 and associated geometric characteristics 413. In one example embodiment herein, the predetermined classifications 411 are classifications of features/objects that should be removed from the frames n' and n−1' by the object filter 410, because they are deemed not helpful for determining whether frames indicate a blink condition. By example and without limitation, in the case of filter 409 of the system 401 for detecting a blink condition, the predetermined classifications 411 may include a dust classification, an eye-lid classification, an eye-lash classification, a vessel classification, a choroidal retinal feature classification, and/or any other predetermined classifications of objects deemed not suitable for detecting a blink condition in the image frames n' and n−1'. Also, the respective geometric characteristics 413 associated with corresponding ones of the predetermined classifications 411, define geometric characteristics associated with those classifications 411. By example only, geometric characteristics 413 associated with a "dust" classification 411, may include an area (e.g., total intensity), width, height, and/or other predetermined dimensions/characteristics, that are associated with dust particles, geometric characteristics 413 associated with a "eye-lid" classification 411, may include an area (e.g., total intensity), width, height, and/or other predetermined dimensions/characteristics, that are associated with eye-lids, and the like.

Other types of geometric characteristics 413 that may be employed by filter 409 may include, by example and without limitation, a spatial extent (e.g., width-to-height ratio relative to center of mass and perimeter length), textural characteristics, distances from a centroid of an object feature to selected directional positions on a bounding box (see, e.g., FIGS. 8a-8d described below), vertical and horizontal extent, area, width and length ratios, perimeter length, a moment about a centroid, and the like. In one non-limiting example embodiment herein, the moment is a $2^{nd}$ moment about the centroid, as described in, by example, https://en.wikipedia.org/wiki/Second_moment_of_area, which is incorporated by reference herein. By virtue of the types of predetermined classifications 411 and geometric characteristics 413 employed by the filter 409, the filter 409 is "tuned" to enable detection of a blink condition (if any) in the frames (e.g., by virtue of a cross-correlation to be described below). Indeed, the characteristics 413 can be effective for enabling distinction between objects that have larger spatial extent but a low pixel count area (i.e., objects that should be retained) and objects that have a lower spatial extent with respect to a pixel count area (i.e., objects that should be removed).

Referring again to FIGS. 4a and 5a, after the frames n' and n−1' are first received by the object filter 410 in step 504, the object filter 410 determines whether any objects that may be included in the frames n' and n−1' are detected, by performing a predetermined object detection technique (step 506). If "no" in step 506, then control passes back to step 501 where the method 500 begins again for a next set of frames n and n−1. If "yes" in step 506, on the other hand, then the object filter 410 determines geometric characteristics associated with the detected object(s) (step 508). As an illustrative, non-limiting example, in step 508 the object filter 410 may calculate, for at least one object detected in step 506, at least one image moment (e.g., a 2nd moment) (wherein, as known in the art, an image moment may be a particular average or weighted average of pixel intensities of the image, or a function of such moments, usually chosen to have some attractive property or interpretation), an area (e.g., total intensity), a centroid thereof, an orientation, width, height, and/or other predetermined characteristics associated with detected object(s).

Based on the geometric characteristics determined (in step 508) for the object(s) detected in step 506, and the geometric constraints 412, the object filter 410 determines whether the object(s) can be classified into one or more of the predetermined classifications 411 (step 510). By example, step 510 may include determining whether the geometric characteristics determined in step 508 correspond sufficiently well (e.g., within a predetermined threshold or range) enough to geometric characteristics 413 associated with a particular predetermined classification 411. If "no" in step 510, then control passes back to step 506 where the method continues in the manner described above to determine whether additional objects may be detected in the frames n' and n−1', as described above. If "yes" in step 510, on the other hand, then control passes through connector A to step 511 of FIG. 5b, where the object filter 410 classifies the object(s) as being within the particular predetermined classification 411. Next, in step 512 the object filter 410 removes from the image frames n' and n−1', any object(s) that were classified in step 511, and thereafter control passes to step 513. In one example embodiment, the removal in step 512 is performed by setting the object(s)' pixel values to 'zero' (or, in the case of a greyscale image, changing a greyscale range). Such removal avoids unwanted objects (e.g., dust) from unduly influencing cross-correlation, which will be described below. Then, a determination is made as to whether any additional object is detected in the images n' and n−1' (step 513). If "yes" in step 513, then control passes back to step 508 of FIG. 5a, where the method then proceeds in the above-described manner. If "no" in step 513, then control passes to step 514, which will be described below.

It should be noted that, in one example embodiment herein, the object filter 410 (and/or filter 409) is pre-trained based on images to learn to detect and classify objects in images in the above-described manner. According to one example embodiment herein, the object filter 410 (and/or filter 409) comprises a convolutional neural network (CNN) (not shown) trained to perform the object detection and classifications, wherein, as known in the art, a CNN can be used for machine learning, and employs a class of deep, feed-forward artificial neural networks that can be used to analyze and classify images. In one example embodiment herein, the CNN includes layers (although this example is not limiting or exclusive) and weights of the CNN are adjusted during training in order to minimize classification errors. According to one non-limiting example embodiment herein, classification of images and/or objects in images is performed in accordance with the techniques described in the publication by S. Mondal et al., entitled "Image Similarity Measurement using Region Props, Color and Texture: An Approach", International Journal of Computer Applications (0975-8887), Vol. 121, No. 22, July 2015, pp. 23-26, which is incorporated by reference herein.

Referring now to FIGS. 8a-8d, those figures depict examples of objects that have been classified as belonging to one or more predetermined classifications 411 in step 511, among other objects. Non-zero pixel value areas are represented by reference numeral 802, whereas zero pixel value areas (i.e., darkened areas outside areas 802) are represented by reference numeral 804. Areas 804 may represent objects that were classified (in step 511) and removed (in step 512) (by, e.g., setting their pixel values to zero), and areas 802 may represent detected objects that were not removed in step 512 (e.g., as a result of, for example, not being classified in step 511). In one example embodiment herein, values of non-zero areas may all have the same value, as in a binary image, or, in other examples, pixels above a particular threshold retain their current greyscale value. As an example in the case of greyscale, if a threshold value of '125' is applied to an object represented as 8-bit greyscale, then values that remain are in the range of '126' to '256'. As such, the object now is represented by the original greyscale values but it is still isolated from its background by pixels set to zero (i.e., all those with values '125' and below).

Figure 8A:
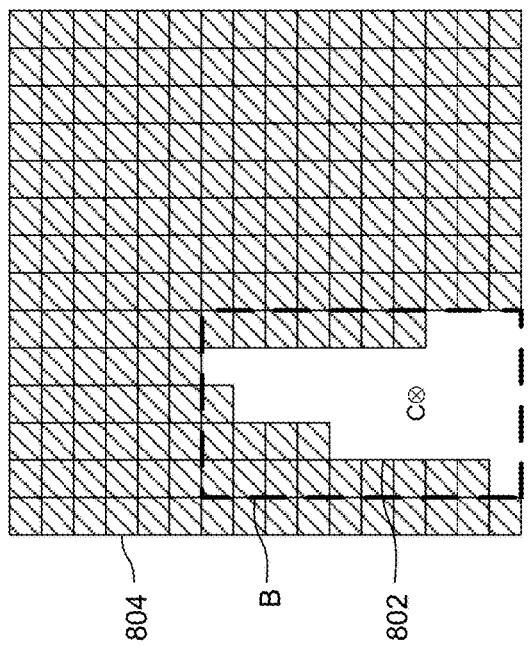
FIG. 8a depicts an example of objects that have been classified as belonging to one or more predetermined classifications.
Figure 8B:
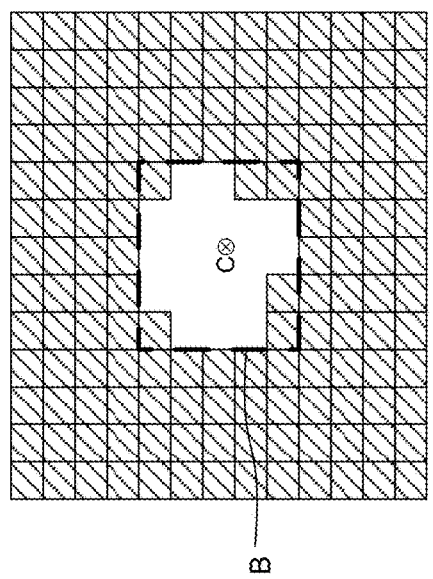
FIG. 8b depicts another example of objects that have been classified as belonging to one or more predetermined classifications.
Figure 8C:
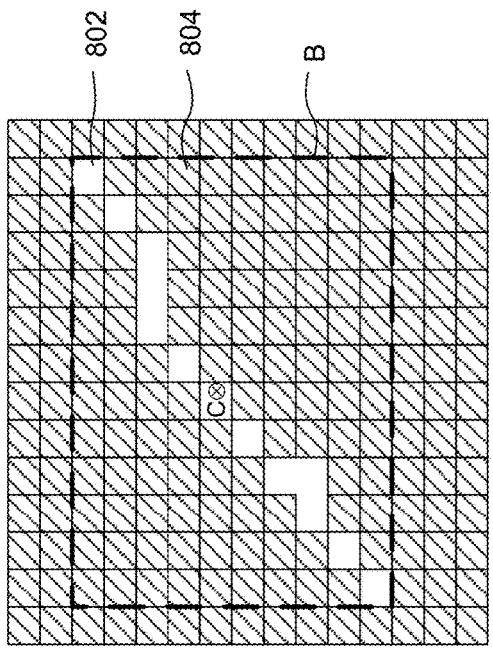
FIG. 8c depicts a further example of objects that have been classified as belonging to one or more predetermined classifications.
Figure 8D:
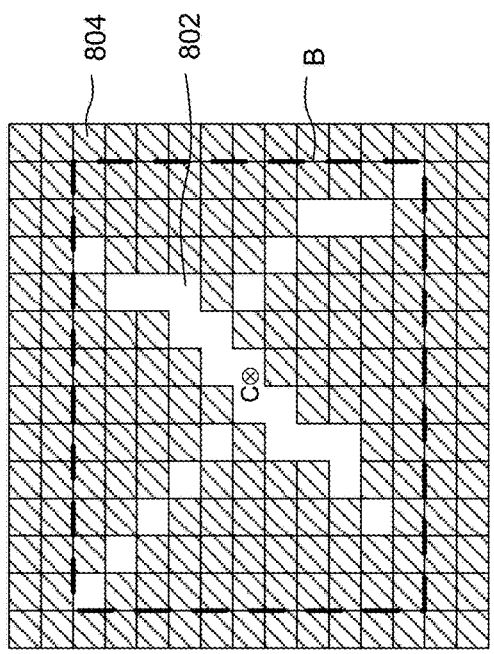
FIG. 8d depicts still another example of objects that have been classified as belonging to one or more predetermined classifications.

Also represented in FIGS. 8a-8d are examples of centroids C, such as those calculated in step 508, and bounding boxes B (i.e., bounding boxes that may have been generated during object detection in step 506). FIGS. 8a and 8b are representative of images that are indicative of blink conditions, and FIGS. 8c and 8d are representative of images that are indicative of non-blink conditions. It is noted that FIGS. 8a-8b may apply with respect to each system 401, 403, 405 of FIGS. 4a-4b and corresponding method, described herein.

Referring again to FIG. 5b, after all objects requiring removal have been removed from the images under consideration in step 512, and no additional objects are detected ("no" in step 513), then resultant filtered frames n" and n-1" are output by the filter 409. Then step 514 is performed. In step 514, the filtered frames n" and n-1" output from the object filter 410 are cross-correlated by a cross-correlator 430. Image cross-correlation is a known method employing tracking and image registration techniques for accurate 2D and 3D measurements of changes in images. In one example embodiment herein, the cross-correlation performed in step 514 establishes correspondence between one frame (e.g., frame n-1"), as a reference image, and another frame (e.g., frame n"), as a sensed image. Cross-correlation can involve shifting one or both of such frames n" and n-1" so that they have matching, corresponding positions, and provides a measure of a degree of similarity between an image and template. In one example embodiment herein, the cross correlator 430 may be included in the registration module 130 described above, and the cross-correlation of step 514 may be performed in accordance with the Padfield publication, although in other examples other types of cross-correlations can be employed, such as that described in the publication by J. P. Lewis, entitled "Fast Normalized Cross-Correlation," In: Vision Interface, 1995, pp. 120-123, which is incorporated by reference herein.

A result of the cross-correlation performed in step 514 is represented by correlation overlay 420 shown in FIG. 4a. The correlation overlay 420 represents the cross-correlated n" and n-1" frames after shifting to corresponding, same positions (i.e., as a result of the cross-correlation step 514), wherein the overlay 420 includes content from both of the frames n" and n-1", including overlapping content 422 (e.g., pixels) from each frame n" and n-1", and non-overlapping content.

Figure 9:
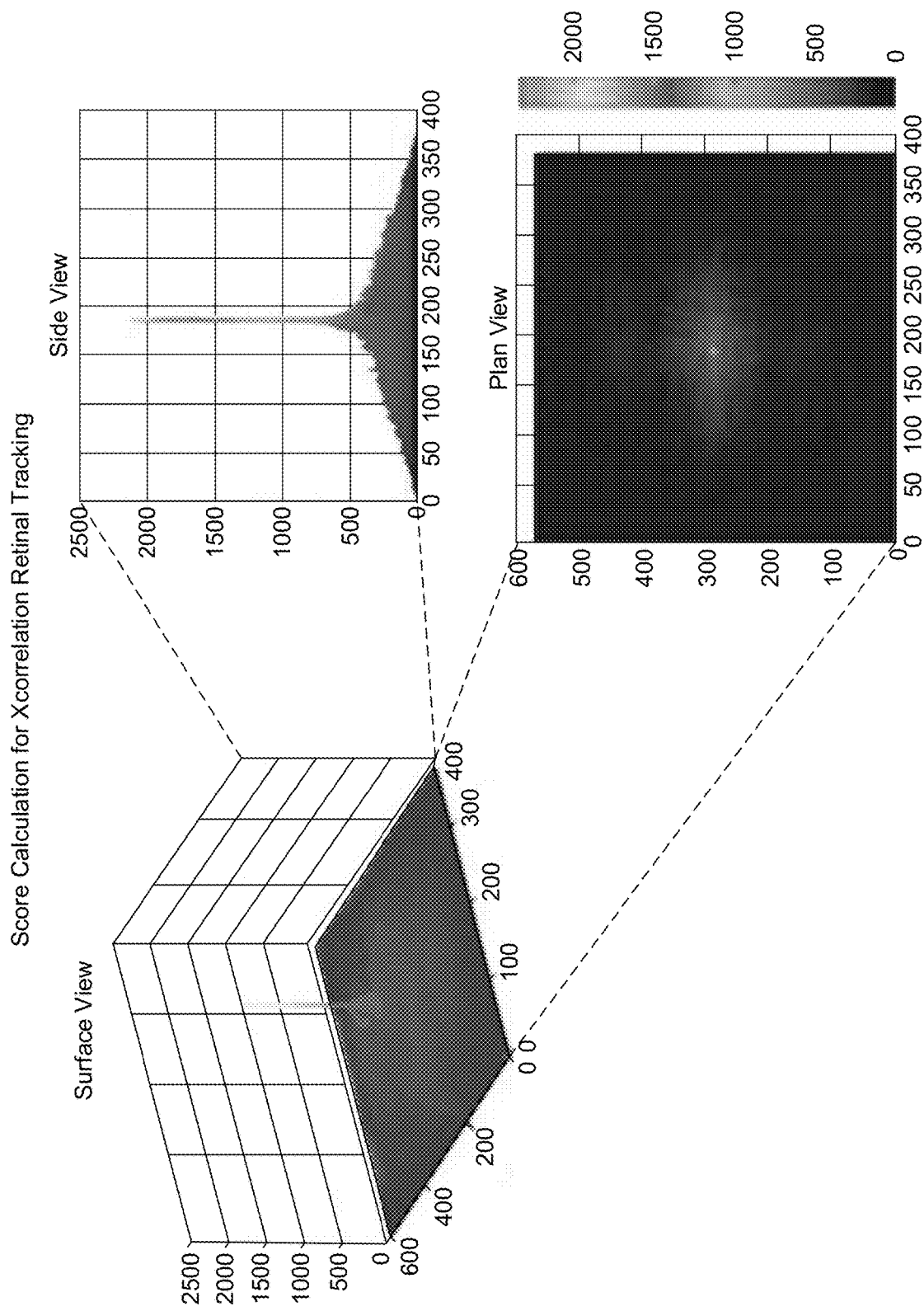
FIG. 9 represents a manner in which a cross-correlation confidence score is calculated, according to an example embodiment herein.

Next, in step 516 a determination is made of a peak characteristic (if any), or score (e.g., a confidence score), relating to the result (correlation overlay 420) of the cross-correlation step 518. In one example embodiment herein, the score is determined by measuring a peak height ratio, weighted by its gradient, over the full cross-correlated frame. By example and without limitation, and referring also to FIG. 9, calculation of a confidence score in step 516 can be performing based on the below formula (F1):

$$\text{confidence score} = \text{round}((A^2/C)*B*D)/S \quad (F1),$$

wherein S is a scaling coefficient (e.g., value '1000'), A represents a peak value minus a next peak value within a predetermined number (e.g., seven) pixel distance in any direction, B represents a gradient of a (+/-3) pixel region around the center of the peak position, C represents a mean value of correlation surface non-zero values excluding the (e.g., seven) pixel region around the peak, and D represents a ratio of a count of zero values in the correlation surface to a total area of the correlation surface, and wherein units in the Surface View, Side View, and Plan View shown in FIG. 9 are in pixels.

In the case of a blink condition present in the frames under consideration, determination of the score in step 516 results in an absence of significant peak characteristics (in one example, such a determination may involve determining that the score is less than a threshold), as represented by correlation surface 432 of FIG. 4a (e.g., the surface 432 may be presented on user interface 280). Such an absence indicates that the blink condition is present in the frames under consideration, and thus the frames (e.g., the IR frame(s), and in some examples, related captured OCT frame(s)) are deemed invalid (i.e., not useful for use in retina tracking) and can be discarded in step 518, so that they are not used in an OCT frame stack. Thus, in one example embodiment herein, in step 518 image frames (n, n-1) for which the score is below the threshold can be discarded, whereas image frames for which the score exceeds the threshold can be maintained. Thereafter, control can pass back to step 501 of FIG. 5a, where the method continues based on a next set of frames.

In another example embodiment herein, instead of classifying and removing objects that are deemed unsuitable for detecting a blink condition (as described above for steps 508-512), detected objects (from step 506 or 513) deemed suitable for detecting the blink condition are classified (in steps 510-511), and those objects are not removed in step 512. Instead, any remaining objects (in the frames under consideration) that were not classified (in steps 510-511) are removed in step 512.

The system 403 (FIG. 4b) and procedure 600 (FIGS. 6a and 6b) will now be described in detail. As explained above, procedure 600 is performed to determine whether an image n has a partial blink condition. In step 600-1, image frame n and a previous frame image n-1 are input to the system 403. In step 601, each frame n and n-1 is segmented into two (preferably vertically partitioned) segments (Region A, Region B), wherein in the case of image frame n, Region A and Region B of image frame n also are referred to herein as image segments S1 and S2, respectively, and, in the case of image frame n-1, Region A and Region B thereof are referred to herein as segments S3 and S4, respectively. Next, in step 602, each of the segments S1-S4 is applied to spatial directional filter 402, which operates in the same manner as described above with respect to FIG. 4a, to filter each segment S1-S4, in order to, for example, remove background lighting, high frequency noise, and/or other predetermined undesired features.

As a result of the frame segments S1-S4 being applied to the filter 402, corresponding filtered segments S1'-S4', respectively, are output from the filter 402, and are then applied to filter 409, which operates in a similar manner as filter 409 of system 401 described above, except that the filter 409 of system 403 is tuned to enable the system 403 to detect a partial blink condition in the segments. More particularly, in the case of the system 403 of FIG. 4b, the predetermined classifications 411 in one example are classifications of features/objects that should be removed from the segments S1'-S4' by the object filter 410, because they are deemed not helpful for determining whether frames indicate a partial blink condition. By example and without limitation, in the case of filter 409 of the system 403, the predetermined classifications 411 may include a dust classification, an eye-lid classification, a vessel classification, a choroidal retinal feature classification, and/or any other predetermined classifications of objects deemed not suitable for detecting a partial blink condition in the segments S1'-S4'. Also in the case of system 403, the respective geometric characteristics 413 associated with corresponding ones of the predetermined classifications 411, define geometric characteristics associated with those classifications 411. By example only, geometric characteristics 413 associated with a "dust" classification 411, may include an area (e.g., total intensity), width, height, and/or other predetermined dimensions/characteristics, that are associated with dust particles (i.e., dust may have thinner dimensional and/or textural characteristics). Geometric characteristics 413 associated with a "eye-lid" classification 411, may include an area (e.g., total intensity), width, height, and/or other predetermined dimensions/characteristics, that are associated with eye-lids, and the like. Other types of geometric characteristics 413 that may be employed by filter 409 may include, by example and without limitation, a spatial extent (e.g., width-to-height ratio relative to center of mass and perimeter length), textural characteristics, distances from a centroid of an object feature to selected directional positions on a bounding box (see, e.g., FIGS. 8a-8d described herein), a moment about a centroid (e.g., a $2^{nd}$ moment), vertical and horizontal extent, area, width and length ratios, perimeter length, and the like. By virtue of the types of predetermined classifications 411 and geometric characteristics 413 employed by the filter 409 of system 403, the filter 409 is "tuned" to enable detection of a partial blink condition in the frames (e.g., by virtue of a cross-correlation to be described below).

Referring again to FIGS. 4b and 6a, after the segments S1'-S4' are first received by the object filter 410 of filter 409 (FIG. 4b) in step 604, the object filter 410 determines whether any objects that may be included in the segments S1-S4' (step 606) are detected, by performing the predetermined object detection technique. If "no" in step 606, then control passes back to step 600-1 where the method 600 begins again for a next set of frames n and n–1. If "yes" in step 606, on the other hand, then the object filter 410 of system 403 determines geometric characteristics associated with the detected objects (step 608). As an illustrative, non-limiting example, in step 608 the object filter 410 of system 403 may calculate, for at least one object detected in step 606, at least one image moment (e.g., a $2^{nd}$ moment) (wherein, as known in the art, an image moment may be a particular average or weighted average of pixel intensities of the image, or a function of such moments, usually chosen to have some attractive property or interpretation), an area (e.g., total intensity), a centroid thereof, an orientation, width, height, and/or other predetermined characteristics associated with detected object(s).

Based on the geometric characteristics determined (in step 608) for the object(s) detected in step 606, and the geometric constraints 412 of system 403, the object filter 410 of system 403 determines whether the object(s) can be classified into one or more of the predetermined classifications 411 (step 610). By example, step 610 may include determining whether the geometric characteristics determined in step 608 correspond sufficiently well enough to geometric characteristics 413 associated with a particular predetermined classification 411. If "no" in step 610, then control passes back to step 606 where the method continues in the manner described above to determine whether additional objects may be detected in the segments S1'-S4'. If "yes" in step 610, on the other hand, then control passes through connector B to FIG. 6b to step 611 where the object filter 410 of system 403 classifies the object(s) as being within the predetermined classification 411. Next, in step 612 the object filter 410 removes from the segments S1'-S4', any object(s) that were classified in step 611, and thereafter control passes to step 613. In one example embodiment, the removal in step 612 is performed by setting the object(s)' pixel values to 'zero' (or, in the case of a greyscale image, changing a greyscale range). Such removal avoids unwanted objects (e.g., dust) from unduly influencing cross-correlation, which will be described below. Then, a determination is made as to whether any additional object is detected in the images n' and n–1' (step 613). If "yes" in step 613, then control passes back to step 608 of FIG. 6a, where the method then proceeds in the above-described manner.

After all objects requiring removal have been removed from the images under consideration in step 612, and no additional objects are detected in step 613 ("no" in step 513), then resultant filtered frames S1"-S4" are output by the filter 409 of FIG. 4b. Then step 614 is performed.

In step 614, segments S1" and S3" output by the object filter 410 of system 403 are cross-correlated using a cross-correlator 430a, and segments S2" and S4" output by the object filter 410 of system 403 are cross-correlated using a cross-correlator 430b. Each cross-correlation performed in step 614 is performed in a similar manner as described above with respect to step 514 of FIG. 5b, including, in the case of cross-correlator 430a, establishing correspondence between one segment (e.g., segment S3"), as a reference image, and another segment (e.g., segment S1'), as a sensed image, and, in the case of cross-correlator 430b, establishing correspondence between one segment (e.g., segment S4"), as a reference image, and another segment (e.g., segment S2"), as a sensed image. Cross-correlation can involve shifting one or both of segments S1" and S3", and shifting one or both of segments S2" and S4", so that the respective segment pairs have matching, corresponding positions, and provides a measure of a degree of similarity between an image and template.

A result of the cross-correlation performed by cross-correlator 430a is represented by correlation overlay 464 shown in FIG. 4b, and a result of the cross-correlation performed by cross-correlator 430b is represented by correlation overlay 466 shown in FIG. 4b. The correlation overlay 464 represents correlated segments S1" and S3" after shifting to corresponding, same positions in step 614, and the correlation overlay 466 represents correlated segments S2" and S4" after shifting to corresponding, same positions in step 614.

Next, in step 616 a determination is made of a peak characteristic, or score, relating the result (correlation overlay 464) of the cross-correlation performed for segments S1" and S3" in step 614, and also a determination is made of a peak characteristic, or score, relating the result (correlation overlay 466) of the cross-correlation performed for segments S2" and S4" in step 614. By example, as in the case of FIG. 4a, in one example embodiment herein each score is determined by measuring a peak height ratio, weighted by its gradient, over the full, corresponding cross-correlated segments, using formula (F1) described above. In the case of correlation overlay 464 (for Region A) in the illustrated example, determination of the score (in one example, such a determination may involve determining that the score exceeds a threshold) results in a significant peak characteristic, as represented by correlation surface 468 of FIG. 4b. In the case of correlation overlay 466 (for Region B), determination of the score (in one example, such a determination may involve determining that the score is less than the threshold) results in an absence of significant peak characteristics, as represented by correlation surface 470 of FIG. 4b. The results indicated by the correlation surfaces 468 and 470 indicate that a partial blink condition is present in the corresponding image frames n and n–1 that were input to the system 430. In step 618 a determination is made whether to keep segments under consideration, for use in creating a final (e.g., OCT) image, and/or whether to discard segments under consideration so they are omitted from creation of the final image. By example, the determination in step 618 can depend on where a location of the scan is and its physical height, in relation to eye motion, and, segments (and/or their corresponding frames) for which the score is below the threshold can be discarded, whereas segments (and/or their corresponding frames) for which the score exceeds the threshold can be maintained, in one example. After segments are maintained and/or discarded in step 618, control passes pass back to step 600-1 of FIG. 6a, where the method 600 continues based on a next set of frames.

It is noted that features (objects) that are not removed by the object filter 410 may still be part of a class that does not move with the retina, and, therefore tracking to these residual features could be potentially problematic. However it is typically the case that when n and n−1 frames are aligned (e.g., by the cross-correlation output) then there is greater alignment between suitable tracking features (those on the retina) than other features. This is because, lids and lashes, for example, frequently are in motion (between the n and n−1 frames) in a way that is non-affine. In other words, they typically do not move on a relative flat plane, and can be commonly seen to move relative to each other, as if gaps between objects are stretched, such that, when affine registration is applied, these objects typically will not overlap. An example of that aspect can be seen by comparing the correlation overlays 464 and 466 of FIG. 4b. As can be seen therein, features remaining after object filtering align in region A (e.g., features which will produce a peak in a correlation surface), but have poor alignment in region B (e.g., which will not contribute to a peak in the correlation surface). Thus, features that move in correspondence as the retina moves (and which are desired to be tracked), and not features associated with an eyelids and eye lashes that can move out of correspondence with the retina (and which are not desired to track), can be distinguished. Indeed, by example and without limitation, eye-lids surface texture, eye-lashes and vessels and choroidal retinal features can be distinguished by selection of constraints 412 that remove most unwanted features, leaving behind residual features, which in general do not contribute to the correlation peak.

In another example embodiment herein, instead of classifying and removing objects that are deemed unsuitable for detecting a partial blink condition (as described above for steps 608-612), detected objects (from step 606 or 613) that are deemed suitable for detecting the partial blink condition are classified (in steps 610-611), and those objects are not removed in step 612. Instead, any remaining objects (in the frames under consideration) that were not so classified (in steps 610-611) are removed in step 612.

It is noted that, in any of the above-described embodiments for detecting the partial blink condition, it may occur that certain features (e.g., eye lash features), if present, would tend to appear more prevalently in the lower segments (e.g., region B) versus in the upper segments (e.g., Region A). Thus, in another example embodiment herein, such knowledge can be considered and employed as a possible characteristic for a feature classification, and/or as a classification itself. By example, such classification(s) can be indicative of a partial blink condition.

Having described the method 600 and system 403 for detecting a partial blink condition in images, the system 405 (FIG. 4c) and procedure 700 (FIGS. 7A and 7B) for detecting a non-blink condition will now be described in detail. The method 700 commences in step 701 with an image frame n and a previously obtained frame n−1 being input to the system 405, as described above. Then in step 702 the frames n and n−1 are applied to a spatial directional filter 402 of system 405, wherein the frames n and n−1 are filtered. The spatial directional filter 402 of system 405 operates in the same manner as described above with respect to FIG. 4a, to filter each image frames n and n−1, in order to, for example, remove background lighting, high frequency noise, and/or other predetermined undesired features.

As a result of the image frames n and n−1 being applied to the filter 402 of system 405, corresponding filtered image frames n' and n−1', respectively, are outputted from the filter 402, and are then applied to filter 409 of system 405. The filter 409 of system 405 operates in a similar manner as filter 409 of system 401 of FIG. 4a described above, except that the filter 409 of system 405 is tuned to enable the system 403 to detect a non-blink condition (if any) in the image frames. More particularly, in the case of the system 405 of FIG. 4c, the predetermined classifications 411 are classifications of features/objects that should be removed from the image frames n' and n−1' by the object filter 410 of system 405, because the features/object are deemed not helpful for determining whether frames indicate a non-blink condition. By example and without limitation, in the case of filter 409 of the system 405, the predetermined classifications 411 may include a dust classification, an eye-lid classification, a vessel classification, a choroidal retinal feature classification, and/or any other predetermined classifications of objects deemed not suitable for detecting a non-blink condition in the image frames n' and n−1'. Also in the case of system 405, the respective geometric characteristics 413 associated with corresponding ones of the predetermined classifications 411, define geometric characteristics associated with those classifications 411. By example only, geometric characteristics 413 associated with a "dust" classification 411, may include an area (e.g., total intensity), width, height, and/or other predetermined dimensions/characteristics, that are associated with dust particles, geometric characteristics 413 associated with a "eye-lid" classification 411, may include an area (e.g., total intensity), width, height, and/or other predetermined dimensions/characteristics, that are associated with eye-lids, and the like. Other types of geometric characteristics 413 that may be employed by filter 409 may include, by example and without limitation, a spatial extent (e.g., width-to-height ratio relative to center of mass and perimeter length), textural characteristics, distances from a centroid of an object feature to selected directional positions on a bounding box (see, e.g., FIGS. 8a-8d described herein), a moment (e.g., a $2^{nd}$ moment) about a centroid, vertical and horizontal extent, area, width and length ratios, perimeter length, and the like. By virtue of the types of predetermined classifications 411 and geometric characteristics 413 employed by the filter 409 of system 405, the filter 409 is "tuned" to enable the system 405 to detect of a non-blink condition (if any) in the frames.

Referring again to FIGS. 4c and 7a, after the image frames n' and n−1' are first received by the object filter 410 of filter 409 (FIG. 4c) in step 704, the object filter 410 determines whether any objects that may be included in the frames n' and n−1' (step 706) are detected, by performing the predetermined object detection technique. If "no" in step 706, then control passes back to step 701 where the method 700 begins again for a next set of frames n and n−1. If "yes" in step 706, on the other hand, then the object filter 410 of system 405 determines geometric characteristics associated with the detected objects (step 708). As an illustrative, non-limiting example, in step 708 the object filter 410 of system 405 may calculate, for at least one object detected in step 706, at least one image moment (e.g., a $2^{nd}$ moment) (wherein, as known in the art, an image moment may be a particular average or weighted average of pixel intensities of the image, or a function of such moments, usually chosen to have some attractive property or interpretation), an area (e.g., total intensity), a centroid thereof, an orientation, width, height, and/or other predetermined characteristics associated with detected object(s).

Based on the geometric characteristics determined (in step 708) for the object(s) detected in step 706, and the geometric constraints 412 of system 405, the object filter 410 of system 405 determines whether the object(s) can be classified into one or more of the predetermined classifications 411 (step 710). By example, step 710 may include determining whether the geometric characteristics determined in step 708 correspond sufficiently well enough to geometric characteristics 413 associated with a particular predetermined classification 411. If "no" in step 710, then control passes back to step 706 where the method continues in the manner described above to determine whether additional objects may be detected in the image frames n' and n−1'. If "yes" in step 710, on the other hand, then control passes through connector C to step 711 of FIG. 7b, where the object filter 410 of system 405 classifies the object(s) as being within the predetermined classification 411. Next, in step 712 the object filter 410 removes from the image frames n' and n−1', any object(s) that were classified in step 711, and thereafter control passes to step 713. In one example embodiment, the removal in step 712 is performed by setting the object(s)' pixel values to 'zero' (or, in the case of a greyscale image, changing a greyscale range). Such removal avoids unwanted objects (e.g., dust) from unduly influencing cross-correlation, which will be described below. Then, a determination is made as to whether any additional object is detected in the images n' and n−1' (step 713). If "yes" in step 713, then control passes back to step 708 of FIG. 7a, where the method then proceeds in the above-described manner.

After all objects requiring removal have been removed from the images under consideration in step 712, and no additional objects are detected in step 713 ("no" in step 713), then resultant filtered frames n" and n−1" are output by the filter 409 of FIG. 4c. Then step 714 is performed. In step 714, the filtered frames n" and n−1" output from the object filter 410 of system 405 are cross-correlated by a cross-correlator 430, in the same manner as described above in connection with FIG. 4a.

A result of the cross-correlation performed in step 714 is represented by correlation overlay 472 shown in FIG. 4c. The correlation overlay 472 represents the correlation of both the n" and n−1" frames after shifting to corresponding, same positions (i.e., as a result of the cross-correlation step 714), wherein the overlay 472 includes content from both of the frames n" and n−1", including overlapping content from each frame n" and n−1", and non-overlapping content.

Next, in step 716 a determination is made of a peak characteristic (if any), or score, relating to the result (correlation overlay 472) of the cross-correlation step 714, in the same manner as described above in connection with FIG. 4a (e.g., formula (F1). In the case of a non-blink condition present in the frames under consideration, determination of the score (which, in one example, can include determining if the score exceeds a threshold) in step 716 results in a significant peak characteristic, as represented by correlation surface 474 of FIG. 4c. A significant peak characteristic indicates that retinal features have been identified in the frames under consideration, in addition to a non-blink condition in the frames, and thus the frames (e.g., the IR frame(s) and/or related OCT frame(s)) are deemed valid, suitable for stable retina tracking, and can be maintained in step 718, so they can be used for inclusion in an OCT frame stack. Thus, in one example embodiment herein, image frames (n, n−1) for which the score exceeds the threshold can be maintained (in step 718), whereas image frames for which the score does not exceed the threshold can be discarded (in step 718). Thereafter, control can pass back to step 701 of FIG. 7a, where the method continues based on a next set of frames.

In another example embodiment herein, instead of classifying and removing objects that are deemed unsuitable for detecting a non-blink condition (as described above for steps 708-712), detected objects (from step 706 or 713) that are deemed suitable for detecting the non-blink condition are classified (in steps 710-711), and those objects are not removed in step 712. Instead, any remaining objects (in the frames under consideration) that were not so classified (in steps 710-711) are removed in step 712.

It should be noted that, although the example embodiments herein are described above as processing image frames n and n−1 from an obtained sequence of "live" image frames, wherein image frame n−1 is deemed a reference image, the scope of the invention is not so limited. Indeed, in another example embodiment herein, processing as described herein also can be performed for reference images that are used to track retina movements against, and such reference image(s) can be employed as image frame n (or, in other example embodiments herein, as frame n−1, or frames n and n−1) in the above-described procedures. Such an embodiment can be employed to detect a blink or non-blink condition in such reference image(s), and to discard any such image(s) deemed to include a blink condition, to ensure that tracking can be performed correctly. In still another example embodiment herein, only the "tracking" type of reference images are processed in the above-described manner (i.e., tracking reference image frames are employed as image frames n and n−1), and "live" image frames are not processed in the above-described manner, although in other example embodiments herein, both tracking reference images and "live" image frames can be processed as described above.

The example aspects described herein avoid limitations, specifically rooted in computer technology, relating to conventional techniques for conducting image scanning in optical scanning environments. Such conventional methods and systems typically were not able to distinguish between scanned images that included captured blink (full or partial blink) conditions and those that do not include such conditions, and thus resulting obtained images (including IR SLO images and OCT images) suffered from deficiencies owing to the captured blink conditions. Additionally, conventional attempts to detect images with blink conditions have proven to be ineffective owing to the images typically having low information content and poor signal-to-noise characteristics. By virtue of the example aspects described herein, on the other hand, imaging processing can be performed in a much less complex manner, and in a manner that requires relatively less computer processing and memory resources than those required by the conventional systems/methods, because images with blink conditions can be detected and discarded without being included in final image processing and formation, thereby enabling imaging evaluations to be performed in a more highly computationally and resource-efficient manner relative to the conventional systems/methods. Also, by virtue of the foregoing capabilities of the example aspects described herein, which are rooted in computer technology, the example aspects described herein improve computers and computer processing/functionality, and also improve the field(s) of at least image processing, SLO, OCT, and data processing, and the processing of functional image data.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment (and can form a memory or store). The program or instructions on the non-transitory machine-accessible medium, machine-readable medium, memory, instruction store, or computer-readable storage device or medium, may be used to program a computer system or other electronic device. The machine- or computer-readable device/medium, memory, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable medium", "machine-accessible medium", "machine-readable medium", "memory", "instruction store", "computer-readable storage medium", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, memory, instruction store(s), or storage device(s), having instructions stored thereon or therein which can be used to control, or cause, a computer or computer processor to perform any of the procedures of the example embodiments described herein. The storage medium/memory/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, memory, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Having now described some illustrative embodiments and embodiments, it is apparent that the foregoing is illustrative and not limiting, having been presented by way of example.

The devices and apparatus described herein may be embodied in other specific forms without departing from the characteristics thereof. The foregoing embodiments are illustrative rather than limiting of the described systems and methods. Scope of the optical systems and apparatuses described herein is thus indicated by the appended claims, rather than the foregoing description, and changes that come within the meaning and range of equivalence of the claims are embraced therein.

What is claimed is:

1. A method for detecting whether an eye blink or non-blink is captured in an image, comprising:
   filtering, from the image, one or more objects that are predicted to be unsuitable for determining whether an eye blink or non-blink is captured in the image, to provide a filtered image, wherein the filtering comprises:
      detecting the one or more objects, in the image,
      determining that the one or more objects belong to one or more predetermined classifications, and
      removing the one or more objects from the image, to provide the filtered image;
   cross-correlating the filtered image with a reference image; and
   determining, based on the cross-correlating, whether the eye blink or non-blink is captured in the image.

2. The method of claim 1, wherein the image and the reference image have been captured by an optical system in sequence while the optical system scans an eye.

3. The method of claim 1, wherein the determining of whether the eye blink or non-blink is captured in the image comprises determining a score based on a result of the cross-correlating.

4. The method of claim 3, wherein the score indicates a presence or absence of a characteristic.

5. The method of claim 4, wherein the characteristic is a peak characteristic.

6. The method of claim 4, wherein the absence of the characteristic indicates that the eye blink is captured in the image.

7. The method of claim 4, wherein the presence of the characteristic indicates that the non-blink is captured in the image.

8. The method of claim 1, wherein the eye blink is a full eye blink or a partial eye blink.

9. The method of claim 1, further comprising performing spatial directional filtering to the image prior to the filtering.

10. The method of claim 1, further comprising segmenting each of the image and the reference image into segments, prior to the filtering.

11. A system for detecting whether an eye blink or no-blink is captured in the image, the system comprising:
   a memory storing a program; and
   a computer processor, operating under the program stored in the memory to perform:
      filtering, from the image, one or more objects that are predicted to be unsuitable for determining whether an eye blink or no-blink is captured in the image, to provide a filtered image, wherein the filtering comprises:
         detecting the one or more objects, in the image,
         determining that the one or more objects belong to one or more predetermine classifications, and
         removing the one or more objects from the image, to provide the filtered image,
      cross-correlating the filtered image with a reference image, and
      determining, based on the cross-correlating, whether the eye blink or non-blink is captured in the image.

12. The system of claim 11, wherein the determining comprises determining a score based on a result of the cross-correlating, and the score indicates a presence or absence of a characteristic.

13. The system of claim 12, wherein the absence of the characteristic indicates that the eye blink is captured in the image.

14. The system of claim 11, wherein the presence of the characteristic indicates that the non-blink is captured in the image.

15. The system of claim 11, wherein the eye blink is a full eye blink or a partial eye blink.

16. The system of claim 11, wherein the computer processor also operates under control of the program to perform spatial directional filtering to the image prior to the filtering.

17. A non-transitory computer-readable medium storing instructions which, when executed by a computer processor, cause the computer processor to perform a method for detecting whether an eye blink or non-blink is captured in the image, the method comprising:
   filtering, from the image, one or more objects that are predicted to be unsuitable for determining whether an eye blink or non-blink is captured in the image, to provide a filtered image, wherein the filtering comprises:
      detecting the one or more objects, in the image,
      determining that the one or more objects belong to the one or more predetermined classifications, and
      removing the one or more objects from the image, to provide the filtered image;
   cross-correlating the filtered image with a reference image; and
   determining, based on the cross-correlating, whether the eye blink or non-blink is captured in the image.

18. The non-transitory computer-readable medium of claim 17, wherein the eye blink is a full eye blink or a partial eye blink.

19. The method of claim 1, further comprising, after the detecting of the one or more objects in the image, determining geometric characteristics associated with the one or more objects, wherein the determining that the one or more objects belong to one or more predetermined classifications comprises determining that the calculated geometric characteristics associated with the one or more objects correspond within a predetermined threshold or range to geometric characteristics associated with the one or more predetermined classifications.

20. The method of claim 1, wherein the predetermined geometric characteristics comprise at least one of:
   at least one image moment associated with the one or more objects;
   an area associated with the one or more objects;
   a centroid of the area;
   an orientation associated with the one or more objects;
   a width associated with the one or more objects; or
   a height associated with the one or more objects.

21. The method of claim 1, wherein the one or more predetermined classifications include at least one of:
   a dust classification, and the geometric characteristics associated with the dust classification include an area or a predetermined dimension associated with dust particles, or
   an eye-lid classification, and the geometric characteristics associated with the eye-lid classification include an area or a predetermined dimension associated with eye-lids.

22. The method of claim 1, wherein the filtering is performed using a convolutional neural network trained to perform the detecting of the one or more objects in the image and the determining that the one or more objects belong to one or more predetermined classifications.

* * * * *